US 12,193,649 B2

(12) United States Patent
Hawker et al.

(10) Patent No.: US 12,193,649 B2
(45) Date of Patent: Jan. 14, 2025

(54) FLUID CONDUIT MODULE FOR ATTACHMENT TO AN ENDOSCOPE

(71) Applicant: MEDITECH ENDOSCOPY LTD, Chesterfield (GB)

(72) Inventors: Michael John Hawker, Ipswich (GB); Peter Ramsey, Chesterfield (GB)

(73) Assignee: MEDITECH ENDOSCOPY LTD, Chesterfield (GB)

(*) Notice: Subject to any disclaimer, the term of this patent is extended or adjusted under 35 U.S.C. 154(b) by 804 days.

(21) Appl. No.: 17/285,306

(22) PCT Filed: Oct. 15, 2019

(86) PCT No.: PCT/GB2019/052932
§ 371 (c)(1),
(2) Date: Apr. 14, 2021

(87) PCT Pub. No.: WO2020/079417
PCT Pub. Date: Apr. 23, 2020

(65) Prior Publication Data
US 2021/0345869 A1    Nov. 11, 2021

(30) Foreign Application Priority Data
Oct. 15, 2018  (GB) ...................................... 1816769
Apr. 18, 2019  (GB) ...................................... 1905578

(51) Int. Cl.
*A61B 1/12*     (2006.01)
*A61B 1/00*     (2006.01)
*A61B 1/015*    (2006.01)

(52) U.S. Cl.
CPC .......... *A61B 1/126* (2013.01); *A61B 1/00103* (2013.01); *A61B 1/00119* (2013.01);
(Continued)

(58) Field of Classification Search
CPC ........... A61B 1/012; A61B 1/015; A61B 1/12; A61B 1/00128; A61B 1/00068;
(Continued)

(56) References Cited

U.S. PATENT DOCUMENTS 5,133,336 A * 7/1992 Savitt ...................... A61B 1/12
                                                    600/103
6,113,571 A * 9/2000 Zinger ............. A61B 17/00491
                                                     604/82
(Continued)

FOREIGN PATENT DOCUMENTS

GB     2503556 A       1/2014
WO    2008122969 A1   10/2008

*Primary Examiner* — Ryan N Henderson
(74) *Attorney, Agent, or Firm* — Hayes Soloway PC

(57) ABSTRACT

This invention relates to a fluid conduit module for attaching a receptacle holding sterile water or detergent to air and water ports of an endoscope. A fluid conduit module comprises a first port for connection to an air line of an endoscope; a second port for connection to a water line of an endoscope; a connector configured to attach said receptacle to the fluid conduit module; a first fluid flow path between the first port and the connector; and a second fluid flow path between the second port and the connector.

16 Claims, 18 Drawing Sheets

(52) U.S. Cl.
CPC ...... *A61B 1/00128* (2013.01); *A61B 1/00137* (2013.01); *A61B 1/00142* (2013.01); *A61B 1/015* (2013.01)

(58) Field of Classification Search
CPC ............ A61B 1/00119; A61B 1/00103; A61B 1/00137; A61B 1/00142; A61M 5/50; A61M 5/5013; A61M 5/502; A61M 5/504; A61M 5/5066; A61M 5/508; A61M 5/5086; A61M 2005/5006; A61M 2005/5026; A61M 2005/5033; A61M 2005/5046; A61M 2005/5053; A61M 2005/506; A61M 2005/5073; A61M 2005/5093
See application file for complete search history.

(56) References Cited

U.S. PATENT DOCUMENTS

| | | | | |
|---|---|---|---|---|
| 6,183,421 | B1 * | 2/2001 | Bobo | A61M 25/10184 |
| | | | | 600/486 |
| 8,454,498 | B2 * | 6/2013 | Cushner | A61B 1/00068 |
| | | | | 600/152 |
| 8,454,499 | B2 * | 6/2013 | Cushner | A61B 1/00119 |
| | | | | 600/152 |
| 8,888,689 | B2 * | 11/2014 | Poll | A61B 1/00142 |
| | | | | 600/156 |
| 9,144,373 | B2 * | 9/2015 | Kaye | A61B 1/00128 |
| 9,211,059 | B2 * | 12/2015 | Drach | A61B 1/00119 |
| 9,392,929 | B2 * | 7/2016 | Bendele | A61B 1/015 |
| 9,801,532 | B2 * | 10/2017 | Bettocchi | A61B 1/12 |
| 2006/0287578 | A1 | 12/2006 | Hamazaki et al. | |
| 2016/0106969 | A1 * | 4/2016 | Neftel | A61M 39/165 |
| | | | | 29/426.1 |
| 2016/0331951 | A1 * | 11/2016 | Sokolov | A61M 39/1011 |
| 2017/0036007 | A1 * | 2/2017 | Hallisey | A61M 39/26 |
| 2017/0036008 | A1 * | 2/2017 | Tsai | A61M 39/1011 |
| 2017/0067586 | A1 * | 3/2017 | Jones | A61M 39/1011 |
| 2021/0371175 | A1 * | 12/2021 | Martella | A61B 1/015 |
| 2022/0032029 | A1 * | 2/2022 | Lazzara | A61M 39/1011 |
| 2022/0040468 | A1 * | 2/2022 | Kreatsoulas | A61M 39/1011 |

* cited by examiner

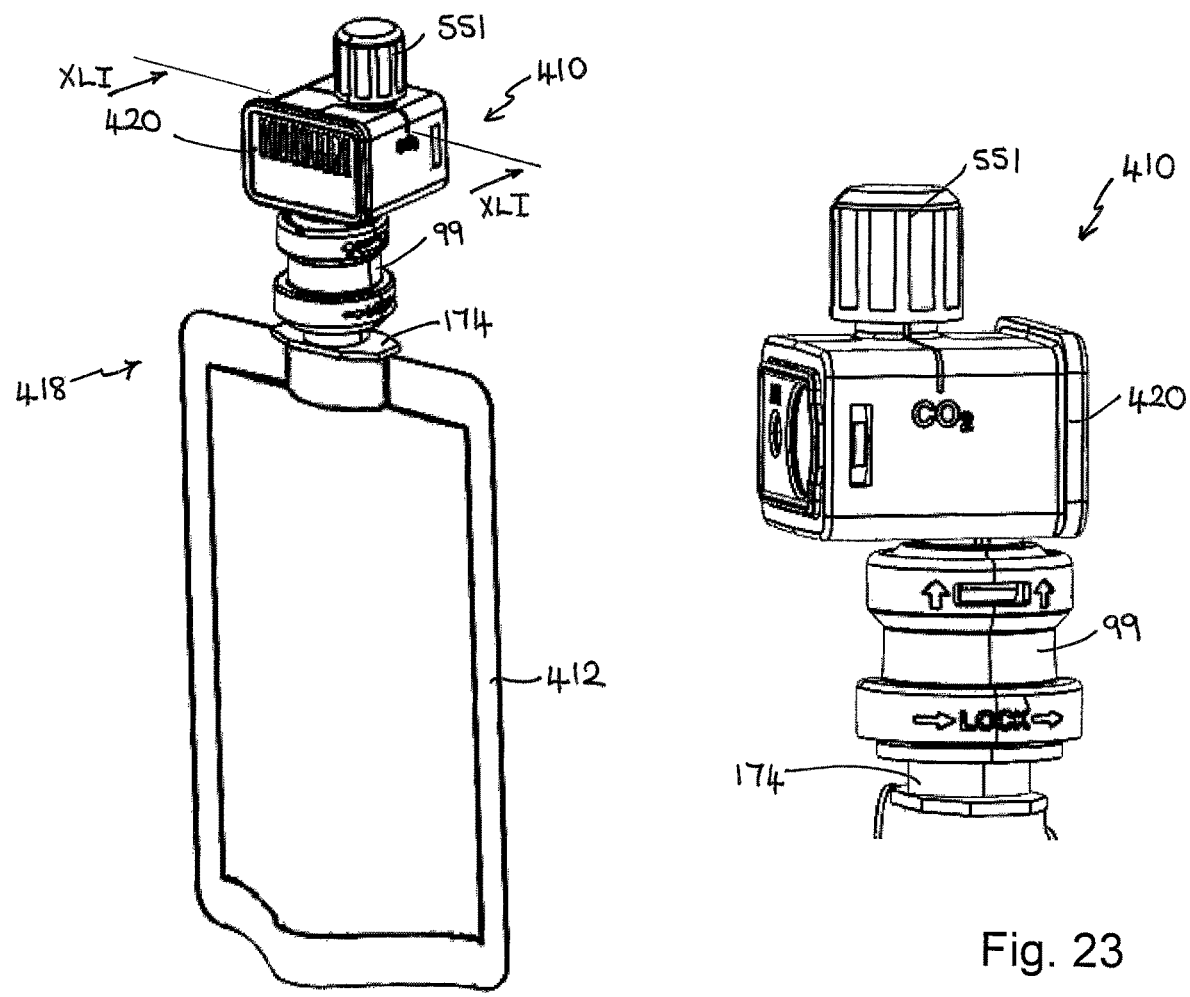
Fig. 22
Fig. 23
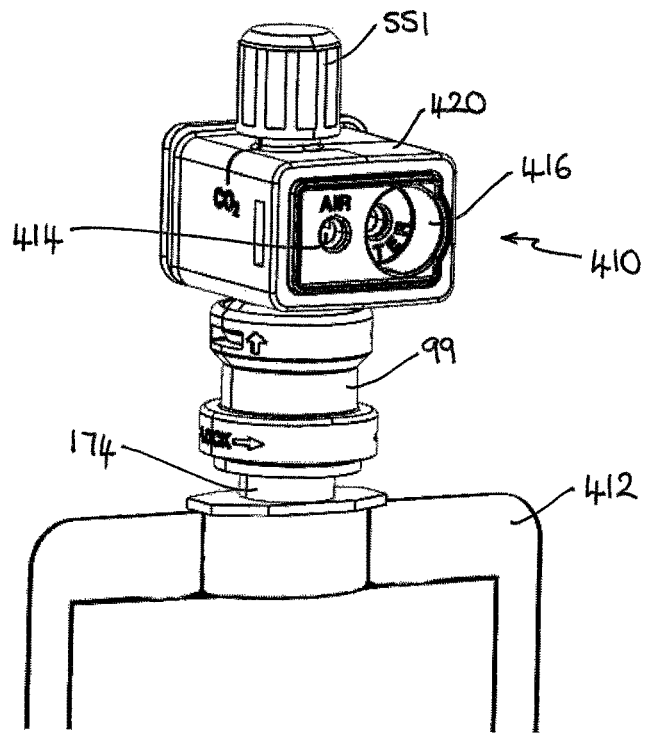
Fig. 24

FLUID CONDUIT MODULE FOR ATTACHMENT TO AN ENDOSCOPE

CROSS-REFERENCE TO RELATED APPLICATIONS AND PRIORITY

This patent application claims priority from PCT Patent Application No. PCT/GB2019/052932 filed Oct. 15, 2019, which claims priority from Great Britain Patent Application No. 1816769.2 filed Oct. 15, 2018 and Great Britain Patent Application No. 1905578.9 filed Apr. 18, 2019. Each of these patent applications are herein incorporated by reference in their entirety.

FIELD OF THE INVENTION

This invention relates to a fluid conduit module for attaching a receptacle to an endoscope. More particularly, this invention relates to a fluid conduit module for attaching a receptacle holding sterile water or detergent to air and water ports of an endoscope. This invention also relates to a container for use with an endoscope, and to a container for storing and delivering sterile water or detergent to an endoscope. This invention further relates to a method of supplying a liquid to a water line of an endoscope using a container according to the invention.

BACKGROUND TO THE INVENTION

Endoscopes are commonly used to provide an internal view of a human or animal body, in particular views of body cavities. Accordingly, endoscopes typically comprise a flexible tube that is inserted into the body. A lens system housed within the flexible tube transmits images from a distal lens at the tip of the tube back to an eyepiece or image sensor at the other end of the tube, to allow an operator to see the internal surfaces and spaces of interest within the body.

Endoscopes generally also include one or more channels through which instruments may be inserted to enable procedures, such as biopsies, to be carried out proximate the tip of the endoscope. These channels also permit fluids including liquids and gasses such as water, air and carbon dioxide, to be delivered through the endoscope. These fluids may be used for irrigation, insufflation or for other purposes, such as rinsing.

It is common during endoscopic procedures for particulate matter present within the body cavity to build up on the lens at the distal end of the endoscope. It is, therefore, necessary to be able to rinse the lens during the procedure to provide an uncompromised view for the operator. This is usually achieved by directing a supply of sterile water across the tip of the endoscope.

Typically, the sterile water is supplied from a separate water bottle that is removeably attached to the endoscope by means of flexible tubing. When the operator wishes to flush the endoscope with water, a button on the endoscope is pressed which directs a flow of air under pressure from the air supply line of the endoscope, through a first flexible tube and into the bottle. This air forces water from the bottle through a second flexible tube and into the water supply line of the endoscope. The water then flows along a channel within the endoscope and is directed across the outer surface of the distal lens to clean it.

Generally the water bottles are mounted at a distance from the endoscope and a relatively long length of flexible tubing connects the water bottle to the endoscope. The flexibility of the tubing means that it is easy to install and remove. Furthermore, having a relatively long length of tubing, in addition to its flexibility provides a tolerance as to where the bottle is positioned relative to the endoscope. It may be necessary in some instances for the bottle to be mounted further from the endoscope than in other instances.

Typically the water bottles contain enough sterile water to be used throughout several endoscopy procedures in a single day; however, the water bottle also provides means for permitting additional sterile water to be added to the bottle if necessary. At the end of the day the bottle and flexible tubing are removed for cleaning and sterilisation. The bottle is then refilled with sterile water the next time it is used.

A major disadvantage of this system is that the water bottle and tubing can become a source of cross-contamination if the bottle and tubing are not cleaned, disinfected, sterilized or dried correctly at the end of the day. If improperly reprocessed, the irrigation water bottle and tubing set can become colonized with *P. aeruginosa* and/or other bacteria during storage, which may then contaminate the sterile water added to the bottle for subsequent endoscopic procedures. Furthermore, there is significant expense, both in terms of time and money, associated with cleaning and sterilising the bottles and tubing used in these procedures.

A known system, designed to reduce the infection risks associated with cleaning and sterilisation, comprises a disposable water bottle cap and flexible tubing assembly. The cap is designed to be secured to a disposable water bottle containing sterile water and the tubing forms a fluid connection between the water bottle and the endoscope. Although these cap and flexible tube assemblies are disposable, they are still designed for 24 hour use and are arranged to be detached from and attached to multiple endoscopes during the day. The flexible tubing, therefore, has at an opposite end to the cap a connector having female air and water ports that connect to the male air and water ports of the endoscope. In this arrangement a first flexible tube extends between the air line of the endoscope and the cap, and a second flexible tube extends from the water line of the endoscope, through the cap and down towards the base of the water bottle. Water is then pumped from the bottle in a similar manner to that described above.

It is also known to provide a single use water bottle for attachment to an endoscope that only contains enough water for a single procedure. The bottles are designed to be disposed of after the procedure. However, these single use water bottles are often refilled with water so that they can be used during multiple procedures, increasing the risk of cross-contamination.

It is an aim of the present invention to provide an improved means for supplying a liquid to an endoscope that overcomes at least some of the disadvantages of prior art systems whether referred to herein or otherwise.

SUMMARY OF THE INVENTION

A first aspect of the present invention provides a fluid conduit module for connecting a receptacle to an endoscope, the receptacle having an internal volume for holding a liquid, and the fluid conduit module comprising:
  a first port for connection to an air line of an endoscope;
  a second port for connection to a water line of an endoscope;
  a connector configured to attach the fluid conduit module to said receptacle;
  a first fluid flow path between the first port and the connector; and a second fluid flow path between the second port and the connector, wherein the connector is configured such that, in use, when a receptacle is connected to the fluid conduit module, the first and second fluid flow paths are in fluid communication with said internal volume of the receptacle, and wherein the fluid conduit module comprises a first single use feature configured to disable the connector to prevent attachment of a second receptacle after use of a first receptacle and a second single use feature configured to hinder or prevent refilling of the receptacle via the first and second flow paths.

The fluid conduit module is preferably configured such that the connector is in a fixed position relative to the first and second ports. The fluid conduit module may be made from a substantially rigid material.

In preferred embodiments the single use feature comprises a weakened part of the connector that is configured to rupture if, in use, a force is applied to the connector to detach the connector from said receptacle. The weakened part of the connector may comprise a thinned section of a side wall of the connector.

In preferred embodiments the connector comprises a screw thread for attachment to a complementary screw thread of said receptacle. In these embodiments the connector preferably comprises a ratchet mechanism configured to allow a receptacle to be secured to the connector but to prevent a receptacle being detached from the connector. The ratchet mechanism is configured such that unscrewing of the receptacle from the connector is hindered or prevented. In this way a user may apply sufficient force to the connector during attempted removal of the receptacle that the weakened part of the connector ruptures or breaks, thereby preventing reuse of the fluid conduit module.

Alternatively or additionally the fluid conduit module may comprise means that hinder or prevent refilling of the receptacle via the first and second flow paths. In preferred embodiments the fluid conduit module comprises a plurality of fluid conduits that are configured such that if a user attempts to inject a liquid through either of the first and second fluid flow paths into the internal volume of the receptacle, the injected liquid is more likely to flow back out through the ports of the fluid conduit module than into the receptacle.

In preferred embodiments the first fluid flow path comprises a first fluid conduit extending between the first port and a closed end and a second fluid conduit extending between a first opening in the connector and a closed end, the second fluid conduit extending substantially perpendicular to the first fluid conduit, and the second fluid flow path comprises a third fluid conduit extending between the second port and a closed end and a fourth fluid conduit extending between a second opening in said connector and a closed end, the fourth fluid conduit extending substantially perpendicular to the third fluid conduit.

Preferably a first intersection permits fluid flow between the first and second fluid conduits, the first intersection being at a distance from the closed end of the first fluid conduit. Furthermore, the first and second fluid conduits are preferably offset such that the direction of fluid flow through the first intersection is substantially perpendicular to axes of both the first and second conduits. Preferably a second intersection permits fluid flow between the third and fourth fluid conduits, the second intersection being at a distance from the closed end of the third fluid conduit.

Furthermore, the third and fourth fluid conduits are preferably offset such that the direction of fluid flow through the second intersection is substantially perpendicular to axes of both the third and fourth conduits.

The closed end of the first fluid conduit is preferably curved and more preferably has a hemi-spherical shape. In other embodiments the closed end of the first fluid conduit may be sloped or chamfered such that an end wall of the conduit is not perpendicular to an axis of the conduit. Similarly, the closed end of the third fluid conduit is preferably curved and more preferably has a hemi-spherical shape. In other embodiments the closed end of the third fluid conduit may be sloped or chamfered such that an end wall of the conduit is not perpendicular to an axis of the conduit.

In these embodiments, therefore, the arrangement of the conduits is such that there is a tortuous first fluid flow path and a tortuous second fluid flow path through the fluid conduit module. This means that it is difficult or impossible to inject a liquid through one or other of the fluid flow paths into the receptacle to refill the receptacle. This means that the fluid conduit module is effectively single use when used together with a receptacle that cannot be removed and replaced.

In preferred embodiments a length of tubing extends from the connector and is in fluid communication with the second fluid flow path. The tubing is arranged to extend into the internal volume of a receptacle attached to the fluid conduit module. The tubing is preferably flexible. The length of the tubing is preferably such that an end of the tubing lies proximate a bottom or lower edge of the receptacle when a receptacle is attached to the fluid conduit module.

The fluid conduit module preferably comprises a main body including first and second apertures and a cover including first and second holes. The main body preferably includes an opening in which the cover is received such that the first hole aligns with the first aperture to form the second port of the fluid conduit module and the second hole aligns with the second aperture to form the first port of the fluid conduit module. In preferred embodiments the main body includes a first sealing surface and a second sealing surface and the cover includes a first seat and a second seat. When the cover is engaged with the main body, a first seal element, such as an O-ring, is preferably disposed between the first seat and the first sealing surface to form a fluid tight seal between the main body and the cover surrounding said aligned first hole and aperture, and a second seal element, such as an O-ring, is preferably disposed between the second seat and the second sealing surface to form a fluid tight seal between the main body and the cover surrounding said aligned second hole and aperture.

The cover preferably comprises a latch member and the main body comprises a latch recess, the latch member being engaged with the latch recess when the cover is received in the opening in the main body. The latch member and latch recess may be arranged such that the latch member cannot subsequently be disengaged from the latch recess.

The fluid conduit module is preferably made from a polymeric material, and may be made from an elastomeric material.

A second aspect of the invention provides a container comprising a fluid conduit module according to the first aspect of the invention and a receptacle secured to the connector of the fluid conduit module.

The receptacle preferably comprises a flexible pouch. An internal volume of the receptacle may contain sterile water or a detergent. A container in which the receptacle contains sterile water may be connected to an endoscope to allow cleaning of the lens of the endoscope during an endoscopic procedure. A container in which the receptacle contains detergent may be connected to an endoscope during cleaning and sterilising of the endoscope to assist with cleaning the water channel of the endoscope.

A third aspect of the invention provides an assembly comprising a container according to the second aspect of the invention and an endoscope, the fluid conduit module being engaged with air and water ports of the endoscope such that the container is solely suspended from the endoscope.

A fourth aspect of the invention provides a method of supplying a liquid to a water line of an endoscope, the method comprising:

attaching a container according to the second aspect of the invention to air and water ports of the endoscope; and flowing air from the air port of the endoscope through first port and the first fluid flow path of the fluid conduit module, and into the internal volume of the receptacle to increase the pressure in the internal volume such that a liquid contained in the receptacle is forced to flow out of the receptacle, through the second fluid flow path and second port of the fluid conduit module, and through the water port into the water line of the endoscope.

The method may further comprise, before attaching the container to the endoscope, securing the fluid conduit module to the receptacle by the connector such that fluid can flow from the first fluid flow path into an internal volume of the receptacle and fluid can flow from the internal volume into the second fluid flow path of the fluid conduit module. In some embodiments the step of securing the fluid conduit module to the receptacle comprises engaging screw threads of the connector with screw threads of the receptacle.

The method may further comprise inserting a sealing element between a main body and a cover of the fluid conduit module such that the sealing element surrounds an aperture in the main body aligned with a hole in the cover, and engaging the cover with the main body of the fluid conduit module to retain the sealing elements between the main body and the cover. The sealing element is arranged to provide a fluid-tight seal between a port of the fluid conduit module, formed by the aligned aperture and hole, and a port of the endoscope.

BRIEF DESCRIPTION OF THE DRAWINGS

The invention will now be further described by way of example only and with reference to the accompanying drawings, in which:

FIG. 22 is a perspective view of a fluid conduit module according to a third preferred embodiment of the present invention attached to a receptacle in the form of a pouch;

FIGS. 23 and 24 are perspective views of the fluid conduit module of FIG. 22;

DESCRIPTION OF THE PREFERRED EMBODIMENTS

Figure 4:
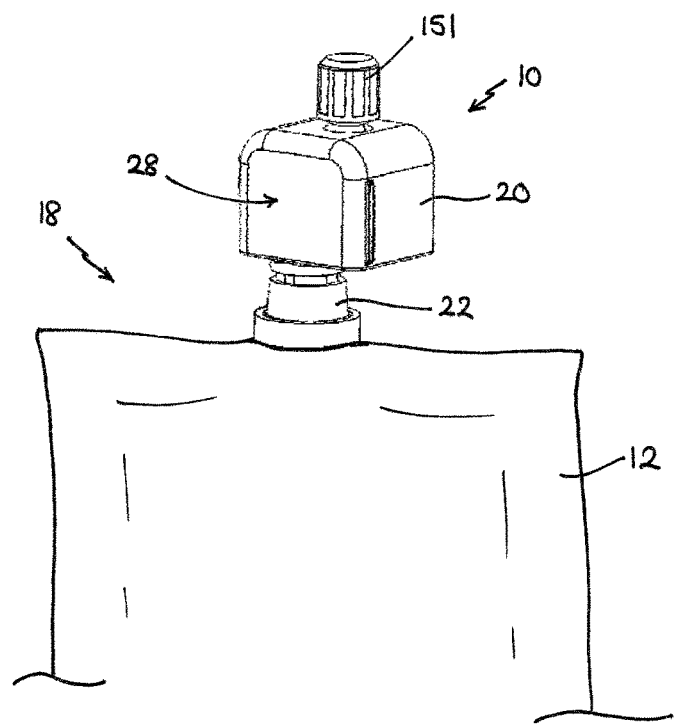
FIG. 4 shows the fluid conduit module of FIG. 1 attached to a receptacle in the form of a pouch to form a complete container according to the present invention.
Figure 5:
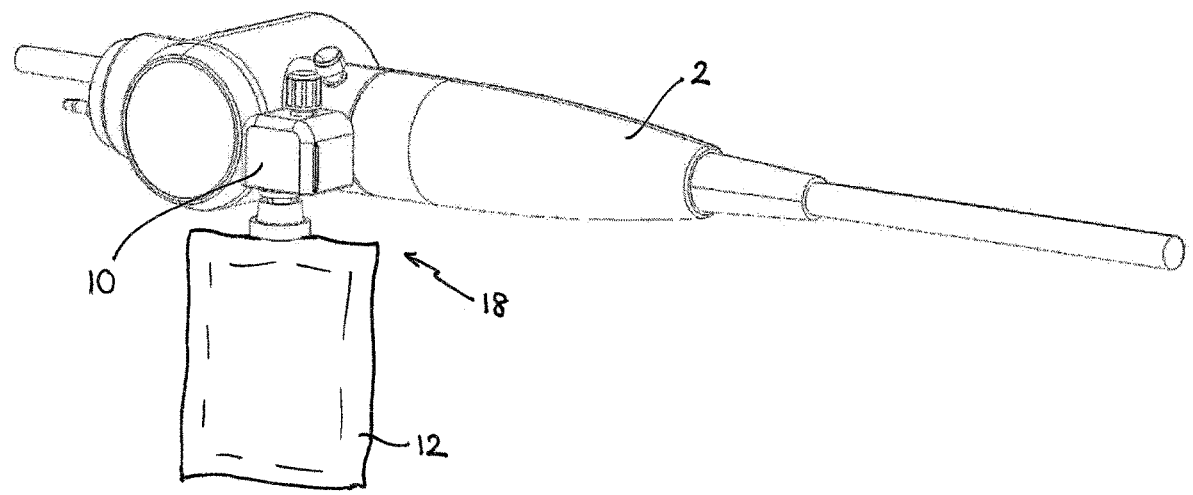
FIG. 5 shows the container of FIG. 4 attached to an endoscope.
Figure 6:
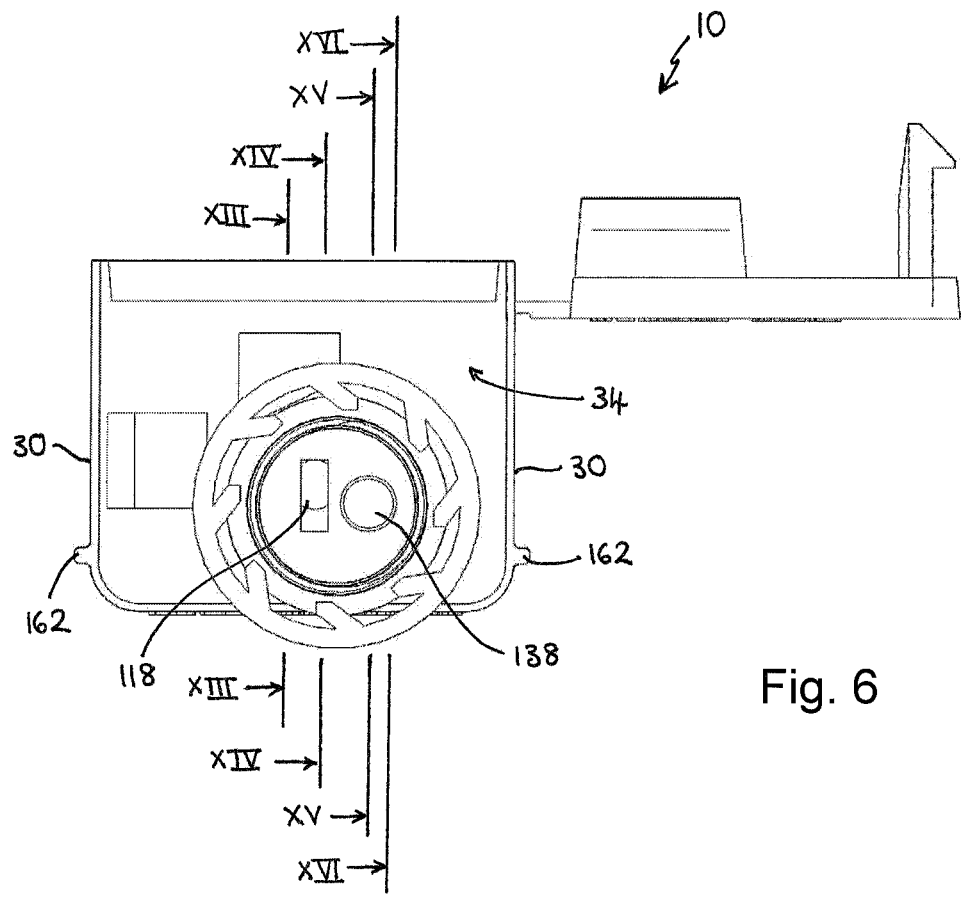
FIG. 6 is a bottom view of the fluid conduit module of FIG. 1.
Figure 7:
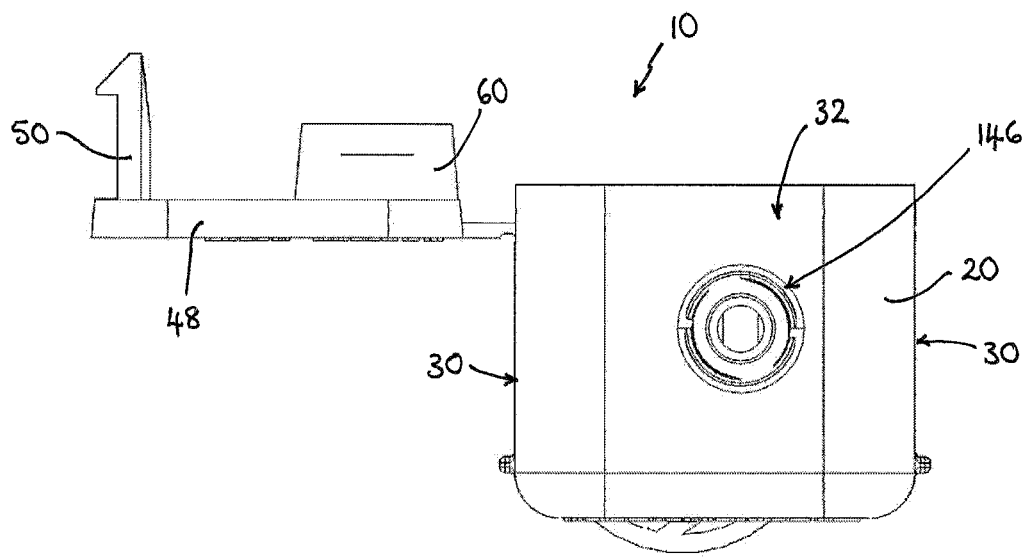
FIG. 7 is a top view of the fluid conduit module of FIG. 1.
Figure 8:
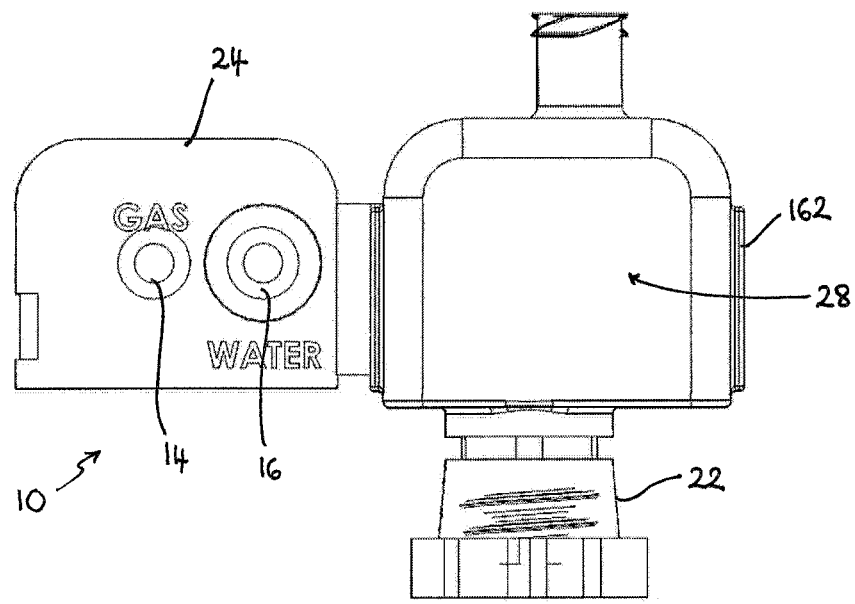
FIGS. 8 and 9 are first and second side views of the fluid conduit module of FIG. 1.
Figure 9:
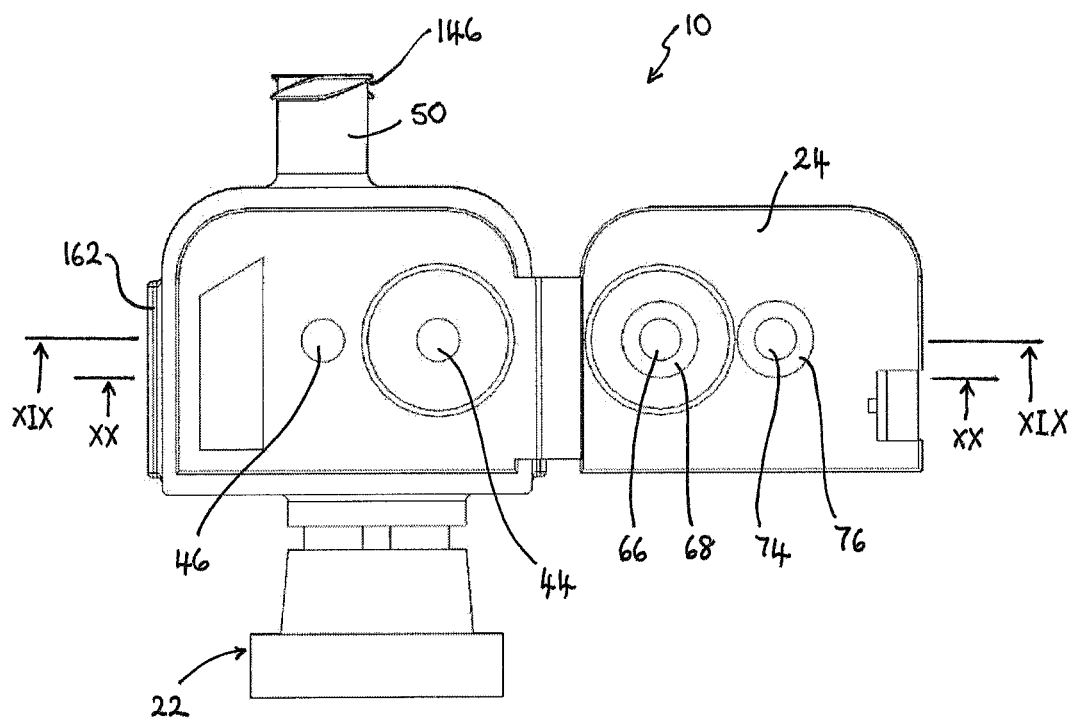
Figure 10:
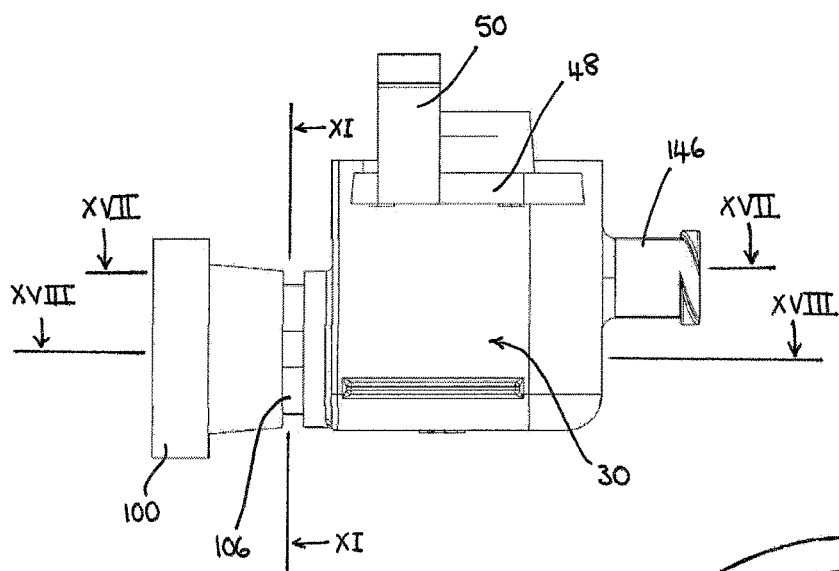
FIG. 10 is a first end view of the fluid conduit module of FIG. 1.

FIGS. 1 to 20 illustrate a fluid conduit module 10 according to a first preferred embodiment of the present invention. The module 10 is configured to attach to a receptacle 12 for holding sterile water or other liquid, such as detergent. In particular, as shown in FIG. 4, the module 10 preferably attaches to a flexible bag or pouch 12 that contains a pre-determined quantity of liquid.

In embodiments in which the pouch contains sterile water, the pouch 12 will typically hold enough water for a single endoscopic procedure. The pouch 12 will typically hold less than 200 ml of water, more preferably between 30 ml and 150 ml. A pouch may hold 50 ml or 100 ml of water. In embodiments in which the pouch contains detergent, the pouch preferably contains enough detergent for a single cleaning operation.

In this embodiment, the fluid conduit module 10 comprises a first port 14 for connection to an air line of an endoscope 2 and a second port 16 for connection to a water line of an endoscope 2. In use, a container 18 comprising the fluid conduit module 10 and the receptacle 12 is attached to an endoscope 2 at or by the ports 14, 16, as show in FIG. 5. The container 18 is, therefore, suspended from the endoscope 2 by the fluid conduit module 10. It will be appreciated that in some embodiments the fluid conduit module may be attached to the endoscope and then a receptacle secured to the fluid conduit module. In other embodiments the complete container will be attached to the endoscope.

During an endoscopic procedure, when a user wishes to rinse the tip of the endoscope 2 using sterile water from the container 18 the user presses a button which forces air from the air line of the endoscope 2, through the first port 14 of the module 10. The air flows through a first set of fluid conduits in the module 10 and into the pouch 12. The increased pressure in the pouch 12 forces water out of the pouch 12 through a second set of fluid conduits in the module 10. The water flows out of the second port 16 and into the water line of the endoscope 2. The water will then flow along channels in the endoscope 2 towards the tip.

In embodiments in which the receptacle 12 is filled with a detergent, it will be appreciated that the container 18 will be attached to the endoscope 2 when a user wishes to clean the water line or water channel of the endoscope 2. In these embodiments, therefore, after the container 18 has been connected to the endoscope 2, the user presses a button which forces air from the air line of the endoscope 2, through the first port 14 of the module 10. The air flows through a first set of fluid conduits in the module 10 and into the pouch 12. The increased pressure in the pouch 12 forces detergent out of the pouch 12 through a second set of fluid conduits in the module 10. The detergent flows out of the second port 16 and into the water line of the endoscope 2. The detergent will then flow along channels in the endoscope 2 towards the tip thereby flushing and cleaning those channels.

The receptacle 12 is preferably pre-filled with a liquid. For example, the fluid conduit module 10 is preferably attached to the receptacle 12 after the internal volume of the receptacle 12 has been filled with the required volume of sterile water or detergent (before or after the fluid conduit module 10 has been attached to the endoscope 2). Once the container 18 has been used in a procedure, the complete container 18 is disposed of. The container 18 is, therefore, single use.

The fluid conduit module 10 is secured to the receptacle 12 in such a way that the fluid conduit module 10 cannot be separated from the receptacle 12 without disabling one or both of the module 10 or the receptacle 12, such that the container 18 cannot be used a second time. This prevents a user removing the fluid conduit module 10 to refill the receptacle 12 so as to use the container 18 multiple times.

In addition, to guard against a user attempting to refill the receptacle 12 by injecting water through the fluid conduit module 10 into the receptacle 12, the fluid conduits in the module 10 are configured in such a way that water will more easily flow back out of the fluid conduit module 10 rather than into the receptacle 12.

With particular reference to FIGS. 1 to 3 and 6 to 12 the fluid conduit module 10 of this embodiment comprises a main body 20, a connector portion 22 and a cover portion 24. In this embodiment the fluid conduit module 10 is a unitary element.

The main body 20 is substantially cuboidal and comprises opposite front and rear faces 26, 28, opposite first and second end faces 30, and opposite top and bottom faces 32, 34. The connector portion 22 extends from the bottom face 34 of the main body 20. In this example, the cover portion 24 is hingedly attached to an edge of the main body 20 between the front face 26 and the first end face 30. The cover portion 24 is moveable between an open position (shown in FIGS. 1 and 2) and a closed position (shown in FIGS. 4 and 5).

A countersunk opening 36 is provided in the front face 26 of the main body 20. The countersunk opening 36 comprises a recess 38 in the front face 26 having a side wall 40 and a base 42. A hole 44 is provided in the base 42 of the recess 38. Preferably the recess 38 and the hole 44 are both substantially circular. The hole 44 is preferably disposed centrally in the base 42.

An aperture 46 is provided in the front face 26 of the main body 20 adjacent the opening 36. The aperture 46 is preferably substantially circular. In preferred embodiments the hole 44 and the aperture 46 are the same size.

The cover portion 24 comprises a cover plate 48 and a latch member 50 extending from the cover plate 48. As shown most clearly in FIG. 20, two holes 52, 54 are formed fully through the cover plate 48 from a first surface 56 of the cover plate 48 to a second surface 58 of the cover plate 48.

An annular wall 60 extends around a first hole 52 in the cover plate 48 and projects from the first surface 56 of the cover plate 48. A cap 62 extends across the hole 52 at a top of the wall 60 furthest from the cover plate 48. A first countersunk hole 64 is provided in the cap 62, such that a first part of the hole 66, nearest the cover plate 48, has a first smaller diameter, and a second part of the hole 68, furthest from the cover plate 48, has a second larger diameter. A shoulder or ledge 70 is, therefore, disposed between the first and second parts of the hole 66, 68. The ledge 70 provides a seat for receiving a seal element such as an O-ring.

A second hole 54 in the cover plate 48 is also countersunk such that a first part of the hole 74, at the second surface 58 of the cover plate 48, has a first smaller diameter, and a second part of the hole 76, at the first surface 56 of the cover plate 48, has a second larger diameter. A shoulder or ledge 78 is, therefore, disposed between the first and second parts of the hole 74, 76. The ledge 78 provides a seat for receiving a seal element such as an O-ring.

When the cover portion 24 is in the closed position the annular wall 60 extends into the recess 38 in the main body 20. Preferably an outer diameter of the annular wall 60 is substantially the same as a diameter of the recess 38. A top surface 80 of the cap 62 preferably contacts the base 42 of the recess 38. An O-ring seated on the ledge 78 is, therefore, confined between the cap 62 and the base 42 of the recess 38. The O-ring extends around and between the hole 44 in the base 42 and the first part of the hole 66 in the cap 62, which are aligned.

Similarly, when the cover portion 24 is closed, the second hole 54 in the cover plate 48 is aligned with the aperture 46 in the main body 20. An O-ring seated on the ledge 78 is, therefore, confined between a part of the cover plate 48 and the front face 26 of the main body 20.

In the closed position the second hole 54 in the cover plate 48 forms the first port 14 of the module 10 for connection to an air line of an endoscope 2 and the hole 64 in the cap 62 forms the second port 16 of the module 10 for connection to a water line of an endoscope 2. The O-rings provide gas and water tight seals between the protruding gas and water ports on the endoscope 2 and the first and second ports 14, 16 of the fluid conduit module 10, respectively.

Figure 20:
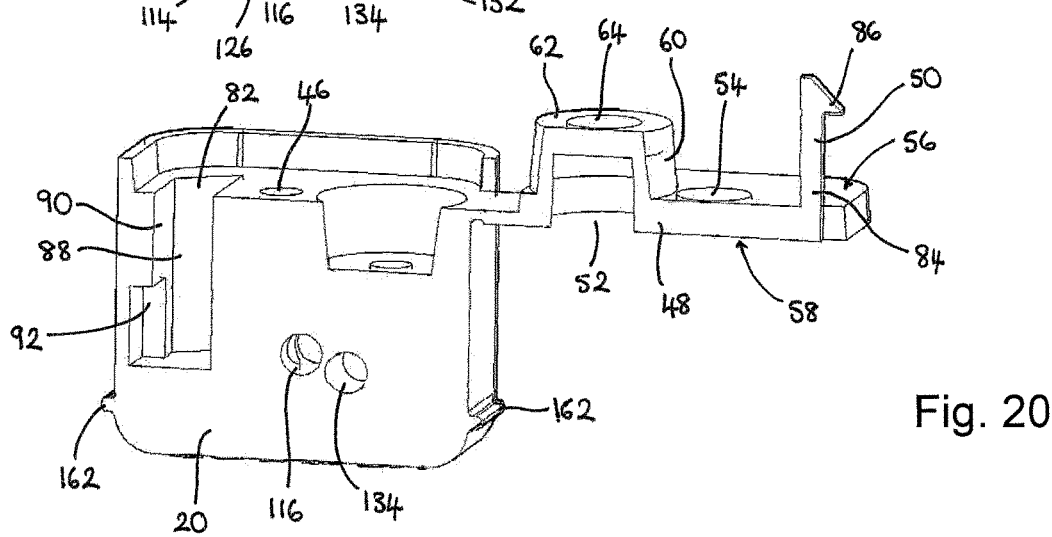
FIG. 20 is a sectioned perspective view along the line XX-XX of FIG. 9.

As shown most clearly in FIG. 20, in this embodiment the main body 20 comprises a latch recess 82 configured to engage with the latch member 50 of the cover portion 24. In this embodiment the latch member 50 comprises a stem 84 extending from the cover plate 48 and a barb 86 disposed at a distal end of the stem 84. The latch recess 82 comprises a channel 88 extending into the main body 20 from the front face 26. The channel 88 is sized to receive the latch member 50. A side wall 90 of the channel 88 includes an undercut 92 for engagement with the barb 86 of the latch member 50. When the cover portion 24 is moved into the closed position, the latch member 50 is inserted into the channel 88. The latch member 50 is resilient such that the barb 86 is biased into engagement with the undercut 92 and secures the cover portion 24 in the closed position, with the first surface 56 of the cover plate 48 in contact with the front face 26 of the main body 20. When the cover portion 24 is in the closed position the channel 88 is not accessible so that the latch member 50 cannot be disengaged from the channel 88. It will be appreciated that in other embodiments different types of latch mechanism may be used to retain the cover portion 24 in the closed position.

In this embodiment a rim 94 extends around the periphery of the front face 26 of the main body 20 and projects from the front face 26. A height of the rim 94 is substantially the same as a thickness of the cover plate 48. When the cover portion 24 is in the closed position the cover plate 48 is received within the rim 94 and the rim 94 extends around and covers a peripheral edge of the cover plate 48.

Figure 1:
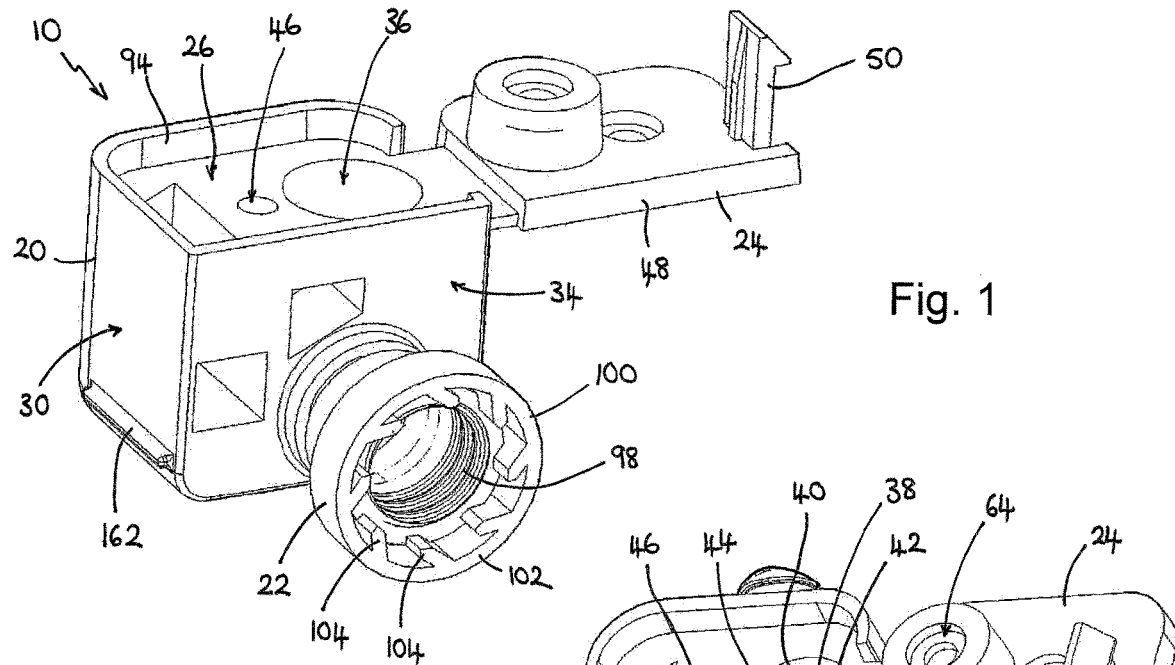
FIG. 1 is a perspective view of a fluid conduit module according to a first preferred embodiment of the present invention.
Figure 2:
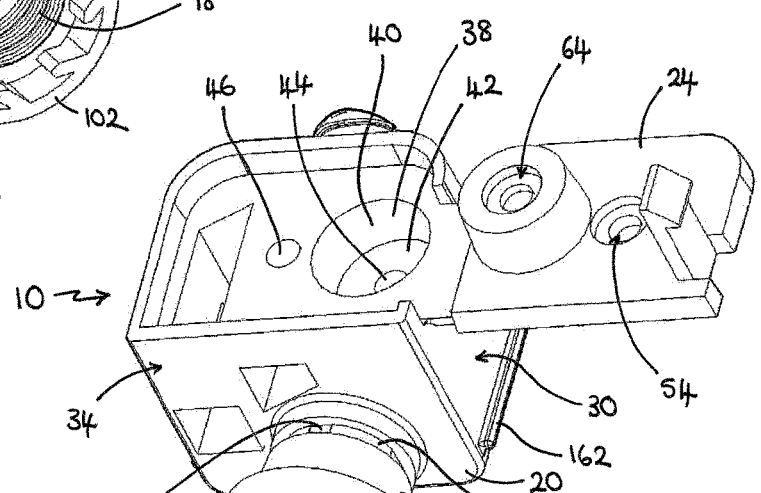
FIG. 2 is a further perspective view of the fluid conduit module of FIG. 1.
Figure 3:
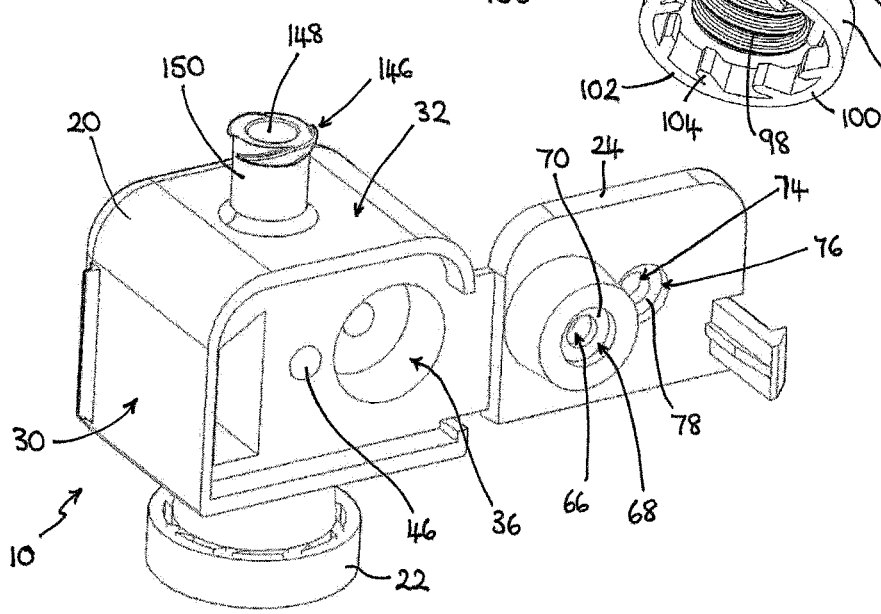
FIG. 3 is a further perspective view of the fluid conduit module of FIG. 1.
Figure 11:
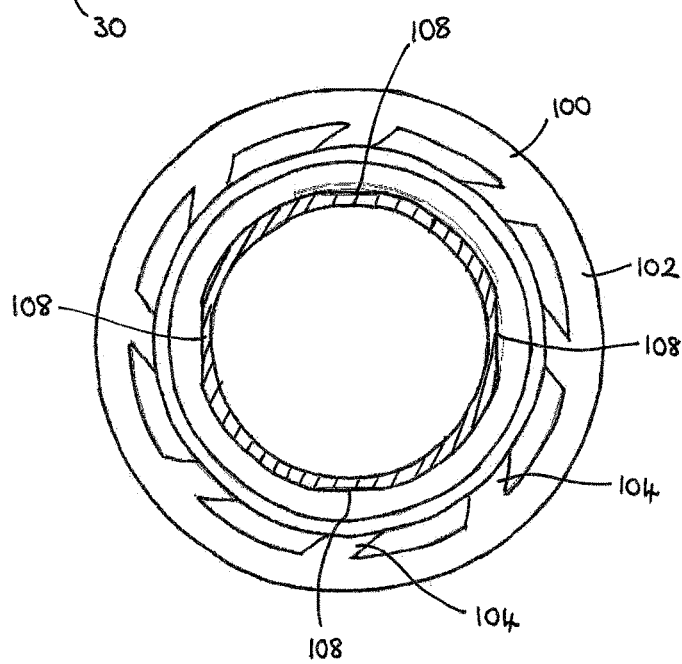
FIG. 11 is a cross-sectional view along the line XI-XI of FIG. 10.
Figure 12:
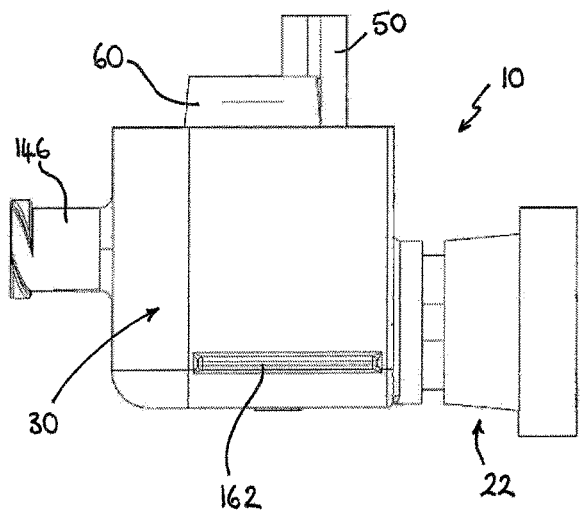
FIG. 12 is a second end view of the fluid conduit module of FIG. 1.
Figure 13:
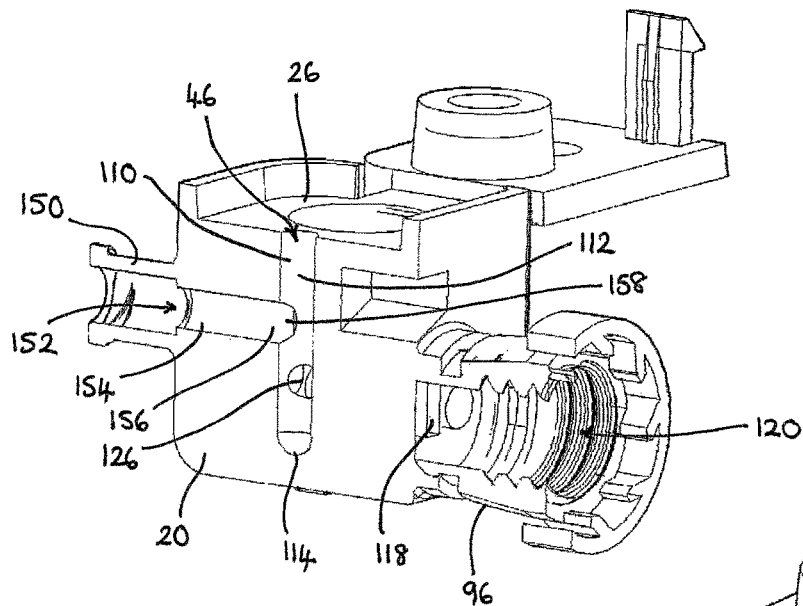
FIG. 13 is a sectioned perspective view along the line XIII-XIII of FIG. 6.
Figure 14:
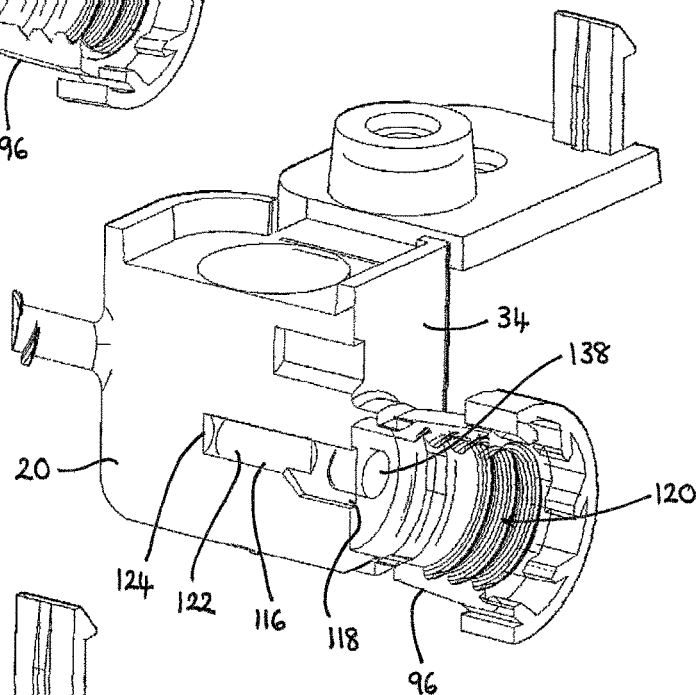
FIG. 14 is a sectioned perspective view along the line XIV-XIV of FIG. 6.
Figure 15:
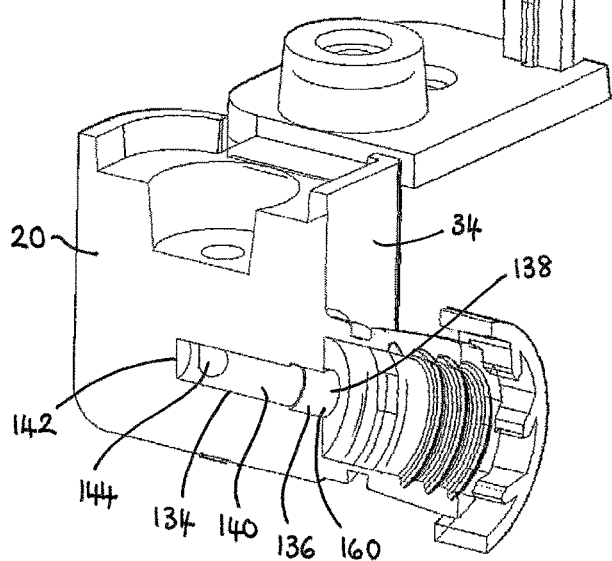
FIG. 15 is a sectioned perspective view along the line XV-XV of FIG. 6.
Figure 16:
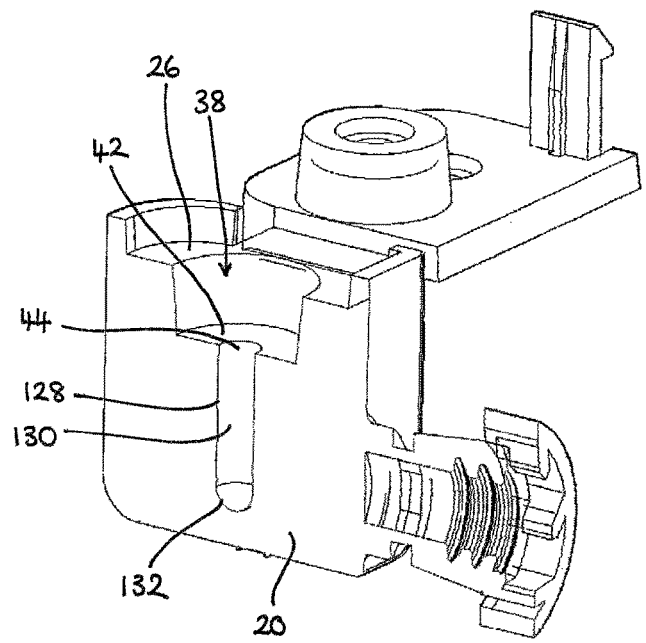
FIG. 16 is a sectioned perspective view along the line XVI-XVI of FIG. 6.
Figure 17:
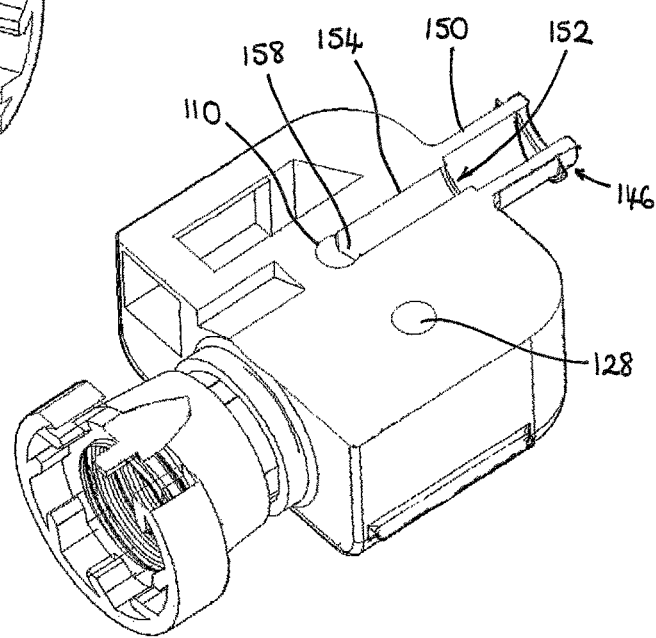
FIG. 17 is a sectioned perspective view along the line XVII-XVII of FIG. 10.
Figure 18:
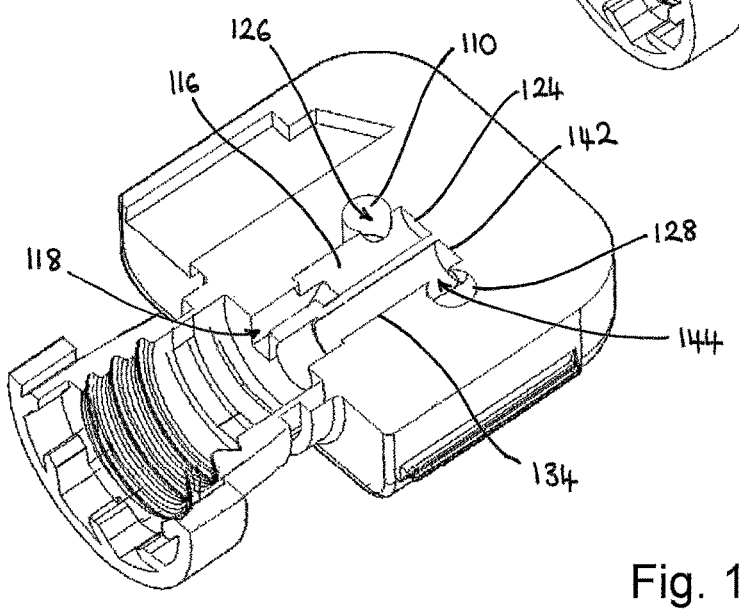
FIG. 18 is a sectioned perspective view along the line XVIII-XVIII of FIG. 10.
Figure 19:
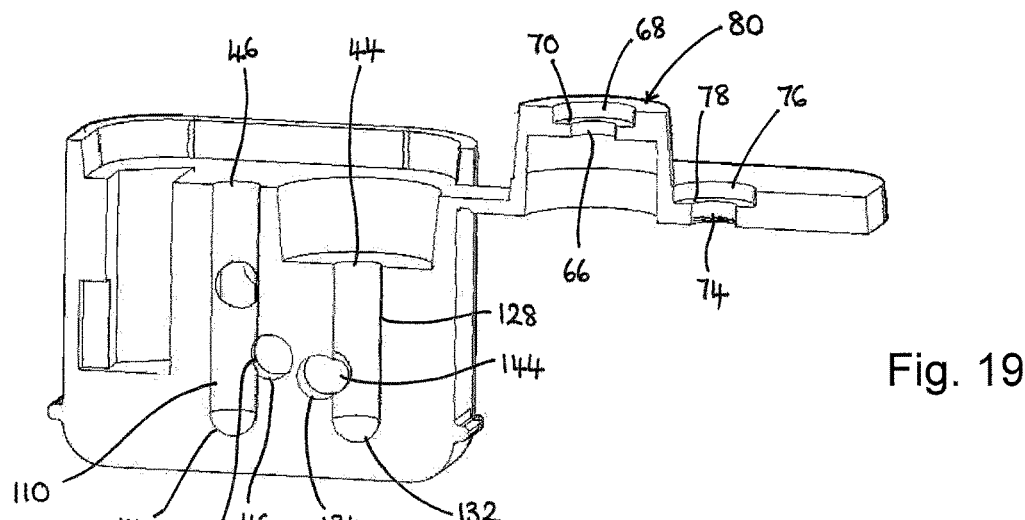
FIG. 19 is a sectioned perspective view along the line XIX-XIX of FIG. 9.

As shown most clearly in FIGS. 1, 2 and 11, the connector portion 22 comprises a tube 96 that extends from the bottom face 34 of the main body 20. An internal surface 98 of the tube 96 is threaded for engagement with a suitable threaded connector on the receptacle 12. In preferred embodiments the bottom face 34 of the main body 20 is perpendicular to the front face 26 of the main body 20.

A ratchet ring 100 is disposed at a distal end of the tube 96. The ratchet ring 100 comprises an annular outer member 102 and a plurality of ratchet teeth 104 that are spaced around the outer member 102 and extend inwardly from the outer member 102. The ratchet teeth 104 extend from the outer member 102 at an angle that is not perpendicular to outer member 102. The angled ratchet teeth 104 permit the connector portion 22 to be screwed onto a corresponding connector of the receptacle 12 but prevent or guard against the connector portion 22 being unscrewed.

In addition a weakened section 106 is provided proximate a proximal end of the tube 96. As shown most clearly in FIG. 11, the weakened section 106 comprises thinned regions 108 of the wall of the tube 96. In this embodiment there are four thinned regions 108.

When a user tries to unscrew the module 10 from the receptacle 12, the ratchet ring 100 hinders rotation of the connector portion 22. If a user applies a greater twisting force to the module 10 to try and unscrew the module 10 from the receptacle 12, the thinned regions 108 of the weakened section 106 break or rupture, such that the module 10 becomes unusable.

These features, therefore, guard against a user removing the module 10 from the receptacle 12 to refill the receptacle 12 and use it a second time. The connector portion 22 is, therefore, single-use.

The configuration of the fluid conduits within the module 10 of this embodiment will now be further described with particular reference to FIGS. 13 to 20.

A first fluid conduit 110 extends through the main body 20 from the aperture 46 in the front face 26. The first fluid conduit 110 extends substantially perpendicular to the front face 26. A bore 112 of the first fluid conduit 110 is closed at a second end 114 furthest from the aperture 46. The second end 114 of the conduit 110 is curved and preferably has a hemi-spherical shape. In other embodiments the closed end of the bore 112 may be sloped or chamfered such that an end wall of the conduit 110 is not perpendicular to an axis of the bore 112.

A second fluid conduit 116 extends through the main body 20 from the bottom face 34 of the main body 20. The second fluid conduit 116 extends substantially perpendicular to the bottom face 34. A first end of the conduit 116 terminates in a first opening 118 in the bottom face 34. The first opening 118 is disposed within a bore 120 of the connector tube 96. A bore 122 of the second fluid conduit 116 is closed at its second end 124 furthest from the opening 118. In this embodiment an end wall of the conduit 116 is substantially perpendicular to an axis of the bore 122.

The second fluid conduit 116 extends through the main body 20 in a direction substantially perpendicular to the first fluid conduit 110. The first and second fluid conduits 110, 116 intersect such that fluid may flow through the first conduit 110 and into the second conduit 116. Importantly, the second fluid conduit 116 is offset from the first fluid conduit 110 such that a part of a side wall of the second fluid conduit 116 intersects a part of a side wall of the first fluid conduit 110. In this way an intersection 126 is formed between the first and second conduits 110, 116 permitting fluid flow between the first and second fluid conduits 110, 116, and the fluid flow through the intersection 126 is substantially perpendicular to the axes of both the first and second conduits 110, 116. The intersection 126 is preferably at a distance from the closed end 114 of the first fluid conduit 110.

A third fluid conduit 128 extends through the main body 20 from the hole 44 in the base 42 of the recess 38. The third fluid conduit 128 extends substantially perpendicular to the front face 26. A bore 130 of the third fluid conduit 128 is closed at a second end 132 furthest from the hole 44. The second end 132 of the conduit 128 has a convex curvature and preferably has a hemi-spherical shape. In other embodiments the closed end 132 of the bore 130 may be sloped or chamfered such that an end wall of the conduit 128 is not perpendicular to an axis of the bore 130. The third fluid conduit 128 preferably extends substantially parallel to the first fluid conduit 110.

A fourth fluid conduit 134 extends through the main body 20 from the bottom face 34 of the main body 20. The fourth fluid conduit 134 extends substantially perpendicular to the bottom face 34. The fourth fluid conduit 134 preferably extends substantially parallel to the second fluid conduit 116. A first end 136 of the conduit 134 terminates in a second opening 138 in the bottom face 34. The second opening 138 is disposed adjacent the first opening 118 and within the bore 120 of the connector tube 96. A bore 140 of the fourth fluid conduit 134 is closed at its second end 142 furthest from the opening 138. In this embodiment an end wall of the conduit 134 is substantially perpendicular to an axis of the bore 140.

The fourth fluid conduit 134 extends through the main body 20 in a direction substantially perpendicular to the third fluid conduit 128. The third and fourth fluid conduits 128, 134 intersect such that fluid may flow through the third conduit 128 and into the fourth conduit 134. Importantly, the fourth fluid conduit 134 is offset from the third fluid conduit 128 such that a part of a side wall of the fourth fluid conduit 134 intersects a part of a side wall of the third fluid conduit 128. In this way an intersection 144 is formed between the third and fourth conduits 128, 134 permitting fluid flow between the third and fourth fluid conduits 128, 134, and the fluid flow through the intersection 144 is substantially perpendicular to the axes of both the third and fourth conduits 128, 134. The intersection 144 is preferably at a distance from the closed end 132 of the third fluid conduit 128.

Attempts to refill the receptacle 12 by injecting liquid into either one of the first and third conduits 110, 128 will result in the liquid being ejected back out of the bore 112, 130 as it rebounds off the closed end 114, 132 of the conduit 110, 128. Furthermore, the offset nature of the intersecting conduits 110, 116, 128, 134 results in it being very difficult to force liquid down one of the second and fourth conduits 116, 134 and into the receptacle 12.

In this embodiment the fluid conduit module 10 further comprises a gas port 146 permitting a gas, such as carbon dioxide ($CO_2$), to be pumped through the fluid conduit module 10.

The gas port 146 comprises an inlet 148 formed by a cylindrical tube 150 extending from the top face 32 of the main body 20. The inlet 148 preferably comprises a closure allowing the inlet 148 to be sealed or closed when not in use. In this embodiment the cylindrical tube 150 is configured to engage with a standard Luer Lock cap 151.

The cylindrical tube 150 surrounds an opening 152 in the top face 32 of the main body 20. A fifth fluid conduit 154 extends through the main body 20 from the opening 152. The fifth fluid conduit 154 extends in a direction substantially perpendicular to the top face 32. Preferably the fifth fluid conduit 154 extends in a direction substantially perpendicular to the first fluid conduit 110. A second end 156 of the fifth fluid conduit 154 intersects the first fluid conduit 110 forming an intersection 158 such that fluid is able to flow from the fifth fluid conduit 154 into the first fluid conduit 110.

The intersection 158 between the fifth and first conduits 154, 110 is preferably offset from the intersection 126 between the first and second conduits 110, 116 along the length of the first conduit 110. Also the fifth and second conduits 154, 116 are preferably offset from each other such the intersection 158 between the fifth and first conduits 154, 110 and the intersection 126 between the first and second conduits 110, 116 are at approximately 90° to each other. In this way attempts to inject water through the gas port 146 into the receptacle 12 will be frustrated by the offset nature of the fifth conduit 154 and the second conduit 116. Water will more readily flow out of the first conduit 110 than flow into the receptacle 12 through the second conduit 116.

In preferred embodiments a length of tubing (not shown) is connected to the bottom face 34 of the main body 20 such that the tubing is in fluid communication with the fourth conduit 134. In particular a bore of the tubing is aligned with the second opening 138 in the bottom face 34 of the main body 20. In this embodiment a proximal end of the tubing is disposed in a counterbore section 160 at the end 136 of the fourth fluid conduit 134. The tubing extends through and out of the bore 120 of the connector. When the fluid conduit module 10 is attached to a receptacle 12, the tubing extends into the interior volume of the receptacle 12. Preferably a distal end of the tubing is disposed near a base or end of the receptacle 12. Preferably the tubing is flexible.

In use, to dispense liquid from the receptacle into the endoscope, air from the air line of the endoscope 2 is forced through the first port 14 of the module 10. The air flows through the first and second fluid conduits 110, 116 in the module 10 and into the receptacle or pouch 12. This increases the pressure in the pouch 12. The pressure will typically increase to a maximum of about 5 psi. The increased pressure forces liquid out of the pouch 12 through the tubing, and through the fourth fluid conduit 134 and the third fluid conduit 128 in the module 10. The liquid then flows out of the second port 16 and into the water line of the endoscope 2. The tubing permits all of the liquid within the pouch 12 to be used as the end of the tubing sits or lies at the base of the receptacle 12.

In this embodiment gripping ribs 162 are provided on the first and second end faces 30 of the main body 20. The ribs 162 extend across the end faces 30 in a direction extending between the top and bottom faces 32, 34. The ribs 162 project from the end faces 30 and provide grip features to assist in gripping the module 10 to remove it from the endoscope 2.

The fluid conduit module 10 is preferably made of polypropylene, but may be made of any suitable polymeric material.

Figure 21:
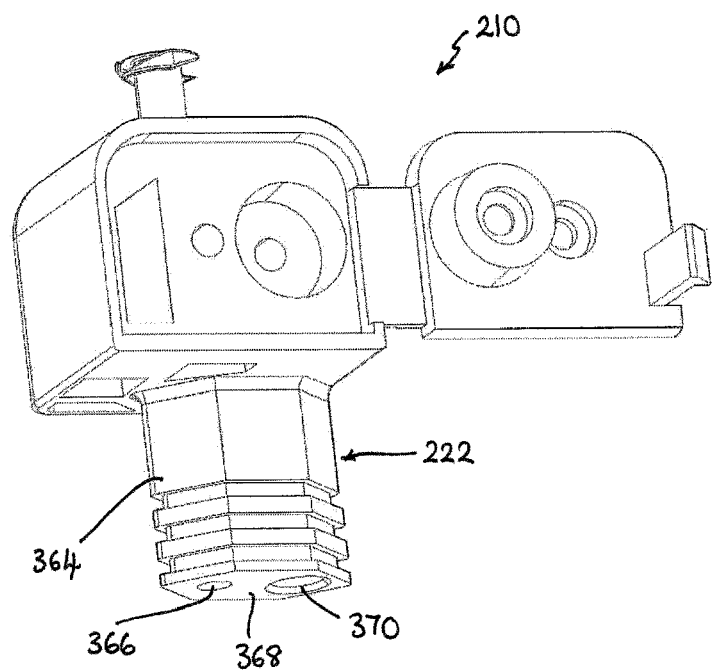
FIG. 21 is a perspective view of a fluid conduit module according to a second preferred embodiment of the present invention.
Figure 25:
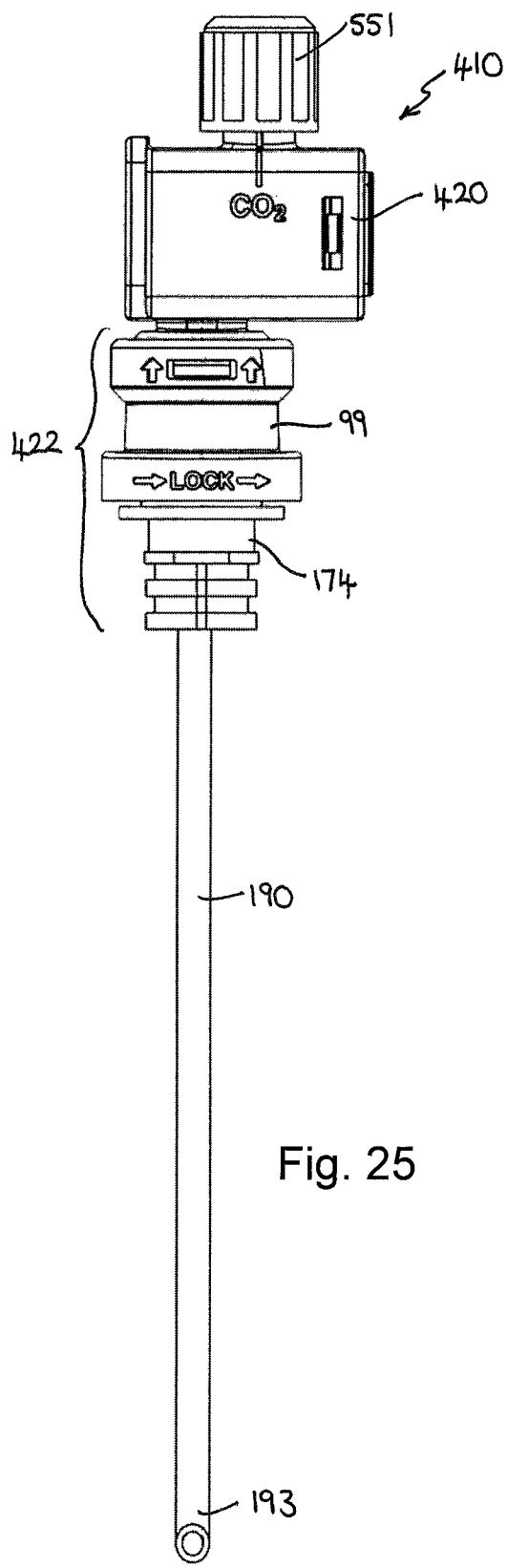
FIG. 25 is a side view of the connector of FIG. 22, with the pouch removed and showing, in particular, a flexible conduit of the fluid conduit module.
Figure 26:
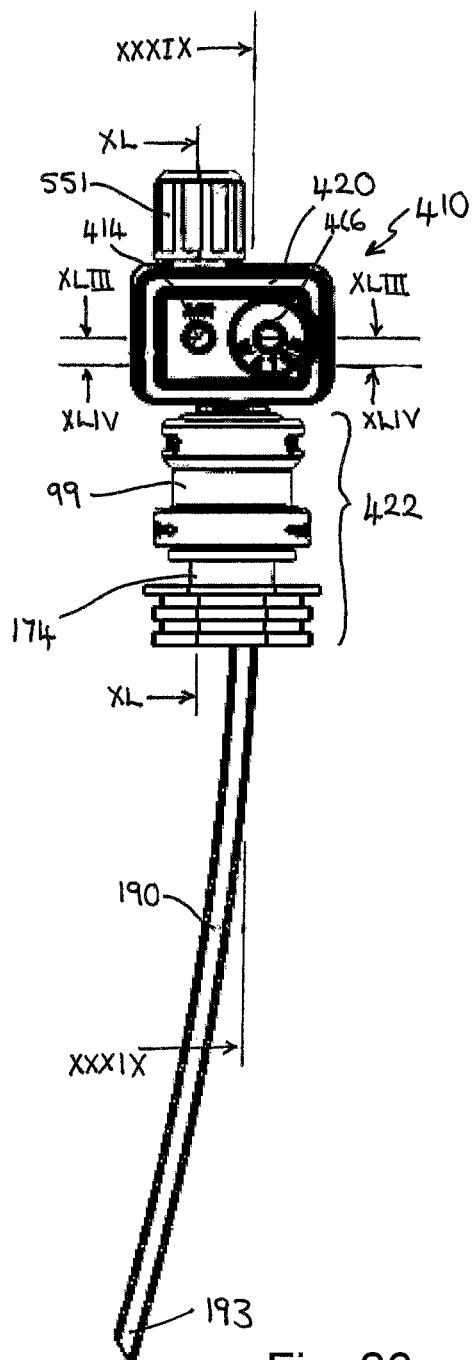
FIG. 26 is a front view of the fluid conduit module of FIG. 25.
Figure 27:
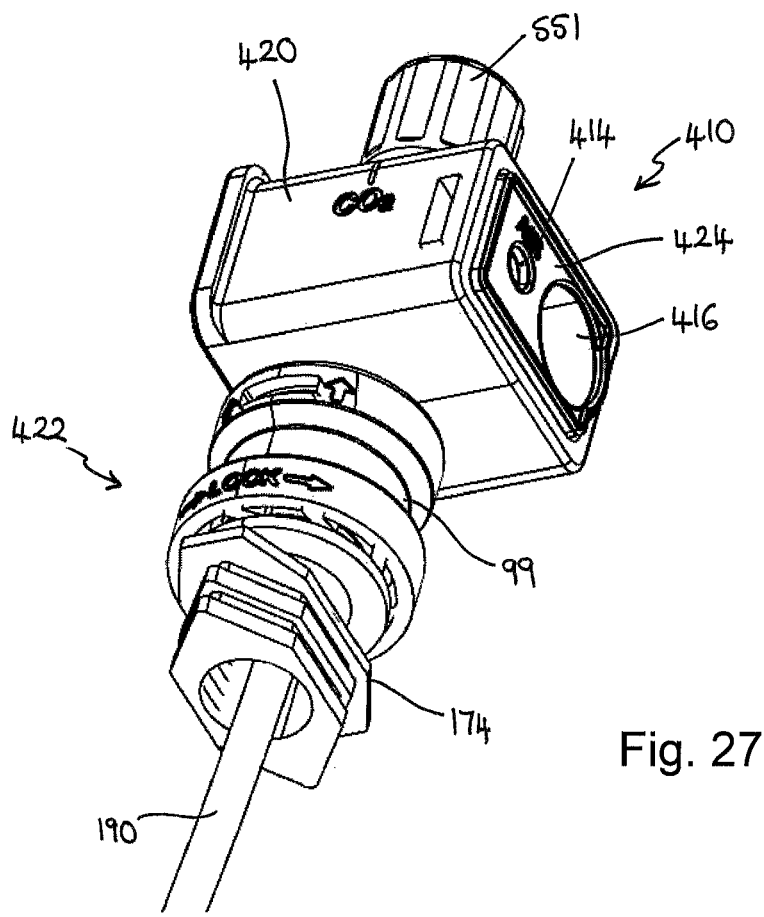
FIG. 27 is a perspective view of a part of the fluid conduit module of FIG. 25.
Figure 28:
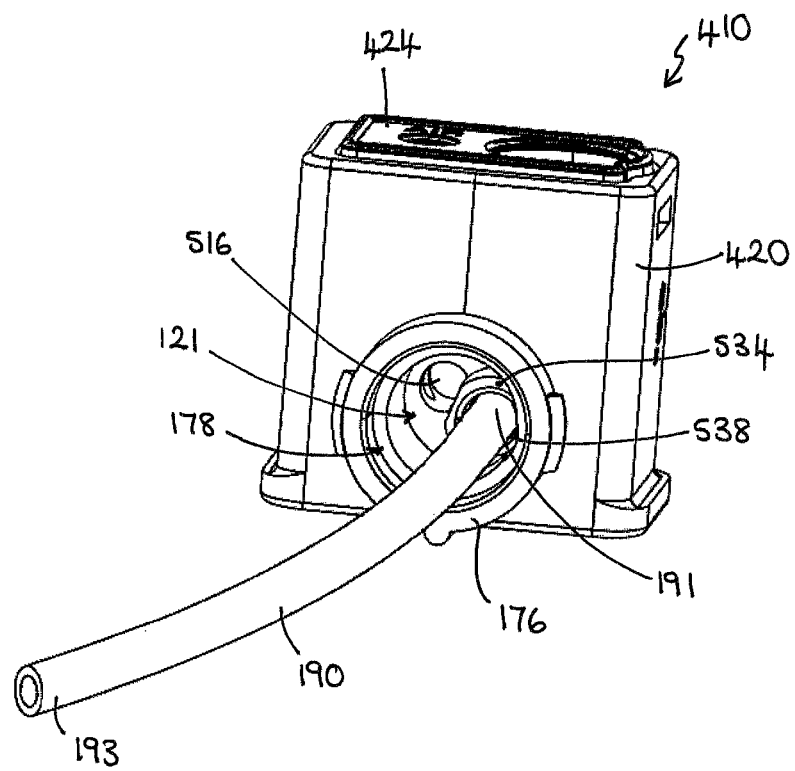
FIG. 28 is a perspective view of the fluid conduit module of FIG. 25.

FIG. 21 shows a second embodiment of a fluid conduit module 210 according to the present invention. Most of the features of the second embodiment are identical to those of the first embodiment and will not be described further here. In particular the internal arrangement of the fluid conduits is identical to that of the first embodiment. Like features are indicated by reference numerals incremented by 200.

This second embodiment has a different connector portion 222 to the first embodiment. The connector portion 22 of the first embodiment was designed to screw onto a receptacle 12 such as a pre-filled pouch which may have previously been closed by a standard screw cap.

In this embodiment the connector portion 222 comprises a spigot or projection 364 configured for attachment to a receptacle such as a flexible pouch. The spigot or projection 364 is preferably configured for heat welding to a flexible pouch.

The second and fourth fluid conduits extend through the connector portion 222. An end of the second fluid conduit terminates at a first opening 366 in a distal end face 368 of the spigot 364. An end of the fourth fluid conduit terminates at a second opening 370 in the distal end face 368 of the spigot 364.

FIGS. 22 to 45 show a fluid conduit module 410 according to a third preferred embodiment of the present invention. Most of the features of the third embodiment are identical to those of the first embodiment and like features are indicated by reference numerals incremented by 400.

The module 410 is configured to attach to a receptacle 412 for holding sterile water or another fluid or liquid, such as a detergent. In particular, as shown in FIGS. 22 and 24, the module 410 preferably attaches to a flexible bag or pouch 412 that contains a pre-determined quantity of liquid. In embodiments in which the pouch contains sterile water, the pouch 412 will typically hold enough water for a single endoscopic procedure. The pouch 412 will typically hold less than 200 ml of water, more preferably between 30 ml and 150 ml. The pouch 412 may hold 50 ml or 100 ml of water. Alternatively the pouch may hold sufficient detergent for a single cleaning procedure. In embodiments in which the pouch contains detergent, the pouch preferably contains enough detergent for a single cleaning operation.

The fluid conduit module 410 comprises a first port 414 for connection to an air line of an endoscope 2 and a second port 416 for connection to a water line of an endoscope 2. In use a container 418 comprising the fluid conduit module 410 and the receptacle 412 is attached to an endoscope 2 at or by the ports 414, 416, as show in FIG. 45. The container 418 is, therefore, suspended from the endoscope 2 by the fluid conduit module 410. It will be appreciated that in some embodiments the fluid conduit module may be attached to the endoscope and then a receptacle secured to the fluid conduit module. In other embodiments the complete container will be attached to the endoscope.

During an endoscopic procedure, when a user wishes to rinse the tip of the endoscope 2 using sterile water from the container 418 the user presses a button which forces air from the air line of the endoscope 2, through the first port 414 of the module 410. The air flows through a first set of fluid conduits in the module 410 and into the pouch 412. The increased pressure in the pouch 412 forces water out of the pouch 412 through a second set of fluid conduits in the module 410. The water flows out of the second port 416 and into the water line of the endoscope 2. The water will then flow along channels in the endoscope 2 towards the tip.

In embodiments in which the receptacle 412 is filled with a detergent, it will be appreciated that the container 418 will be attached to the endoscope 2 when a user wishes to clean the water line or water channel of the endoscope 2. In these embodiments, therefore, after the container 418 has been connected to the endoscope 2, the user presses a button which forces air from the air line of the endoscope 2, through the first port 414 of the module 410. The air flows through a first set of fluid conduits in the module 410 and into the pouch 412. The increased pressure in the pouch 412 forces detergent out of the pouch 412 through a second set of fluid conduits in the module 410. The detergent flows out of the second port 416 and into the water line of the endoscope 2. The detergent will then flow along channels in the endoscope 2 towards the tip thereby flushing and cleaning those channels.

The receptacle 412 is preferably pre-filled with a liquid. For example, the fluid conduit module 410 is preferably attached to the receptacle 412 after the internal volume of the receptacle 412 has been filled with the required volume of sterile water or other liquid (before or after the fluid conduit module 410 has been attached to the endoscope 2). Once the container 418 has been used in a procedure, the complete container 418 is disposed of. The container 418 is, therefore, single use.

The fluid conduit module 410 is secured to the receptacle 412 in such a way that the fluid conduit module 410 cannot be separated from the receptacle 412 without disabling one or both of the module 410 or the receptacle 412, such that the container 418 cannot be used a second time. This prevents a user removing the fluid conduit module 410 to refill the receptacle 412 so as to use the container 418 multiple times.

In addition, to guard against a user attempting to refill the receptacle 412 by injecting water through the fluid conduit module 410 into the receptacle 412, the fluid conduits in the module 410 are configured in such a way that water will more easily flow back out of the fluid conduit module 410 rather than into the receptacle 412.

With particular reference to FIGS. 25 to 28, 39 and 41, the fluid conduit module 410 of this embodiment comprises a main body 420, a connector assembly 422 and a cover 424.

The main body 420 is substantially cuboidal and comprises opposite front and rear faces 426, 428, opposite first and second end faces 430, and opposite top and bottom faces 432, 434. The connector assembly 422 extends from the bottom face 434 of the main body 420. In this example, the cover 424 is received in and engaged with an opening 95 in the front face 426 of the main body 420, shown most clearly in FIG. 32.

Figure 33:
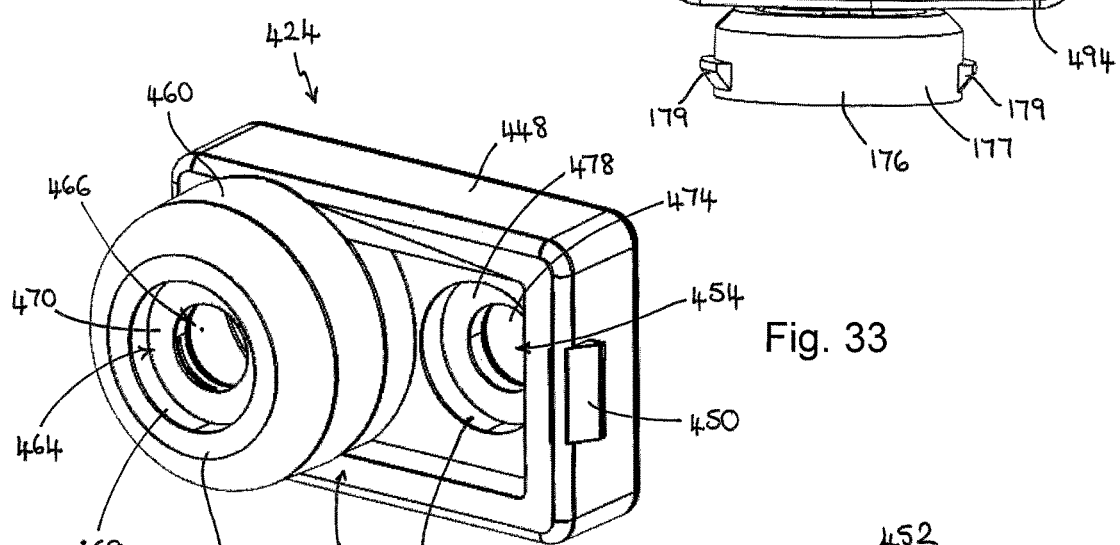
FIGS. 33 and 34 are perspective views of a cover of the fluid conduit module of FIG. 22.
Figure 34:
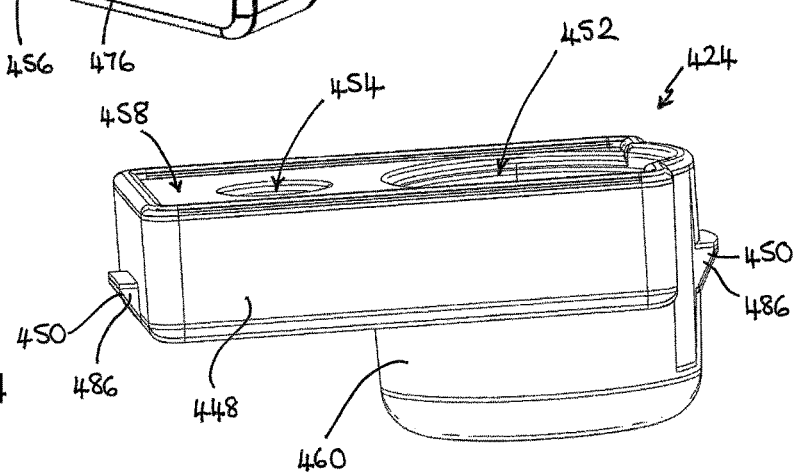
Figure 35:
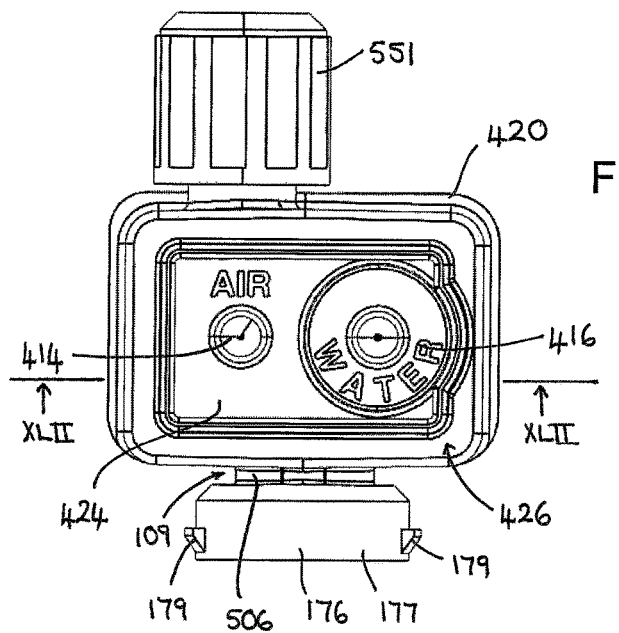
FIG. 35 is a front view of the main body and cover of the fluid conduit module of FIG. 22, the cover being attached to the main body to form ports of the fluid conduit module.
Figure 36:
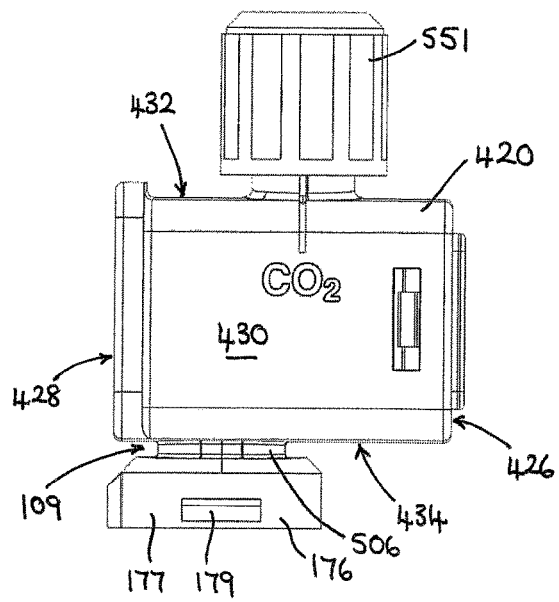
FIG. 36 is a side view of the main body of FIG. 35.
Figure 37:
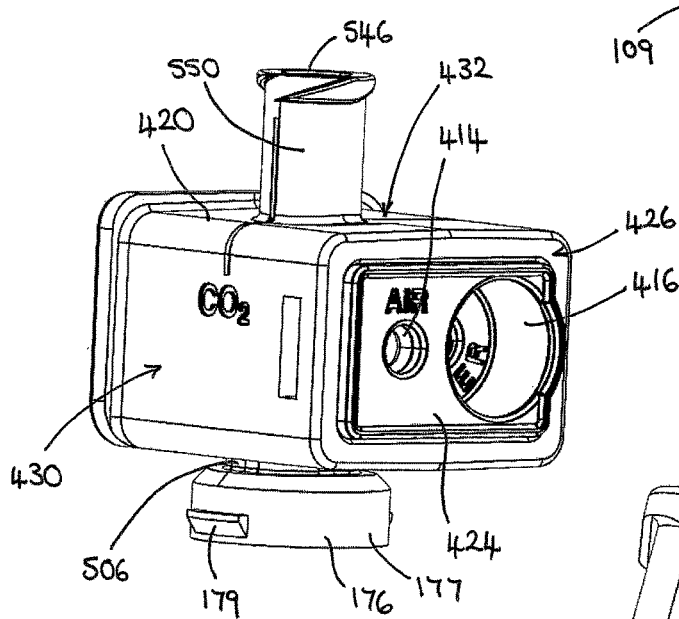
FIGS. 37 and 38 are perspective views of the main body and cover of FIG. 35.
Figure 38:
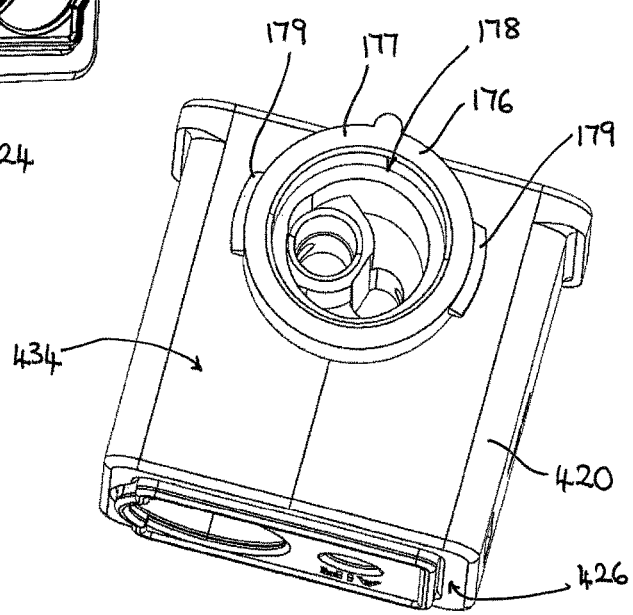
Figures 39, 40:
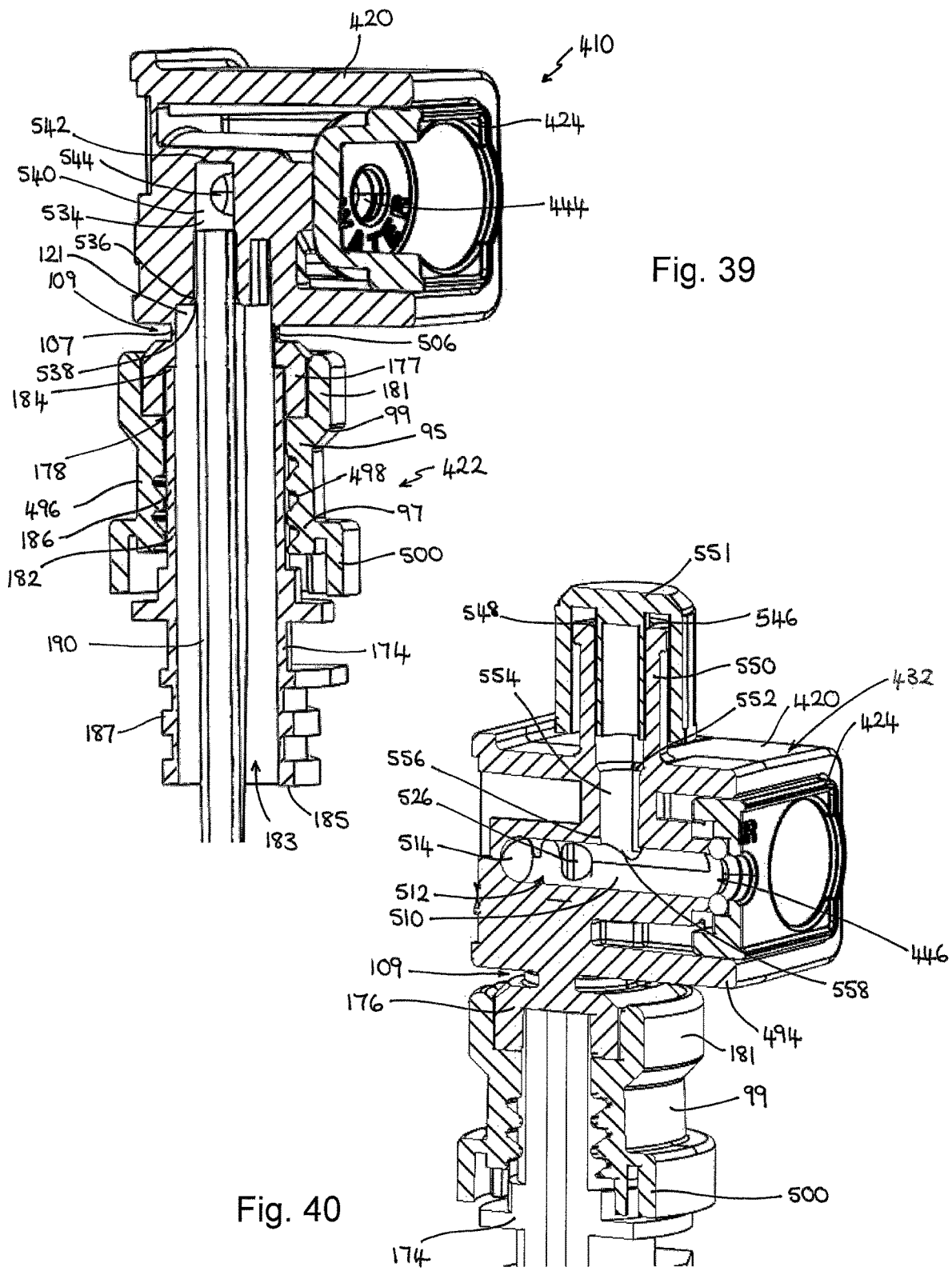
FIG. 39 is a sectioned perspective view along the line XXXIX-XXXIX of FIG. 26.
FIG. 40 is a sectioned perspective view along the line XL-XL of FIG. 26.

The cover 424 comprises a cover plate 448 and a pair of latch members 450 extending from the cover plate 448, as shown most clearly in FIGS. 33 and 34. Two holes 452, 454 are formed fully through the cover plate 448 from a first surface 456 of the cover plate 448 to a second surface 458 of the cover plate 448.

An annular wall 460 extends around a first hole 452 in the cover plate 448 and projects from the first surface 456 of the cover plate 448. A cap or end plate 462 extends across the hole 452 at a top of the wall 460 furthest from the cover plate 448. A hole 464 is provided in the cap 462, and a first part of the hole 466, nearest the cover plate 448, has a first smaller diameter, and a second part of the hole 468, furthest from the cover plate 448, has a second larger diameter. A shoulder or ledge 470 is, therefore, disposed between the first and second parts of the hole 466, 468. The ledge 470 provides a seat for receiving a first seal element such as an O-ring 71, as shown most clearly in FIG. 43.

The second hole 454 in the cover plate 448 also has a first part 474, at the second surface 458 of the cover plate 48, having a first smaller diameter, and a second part 476, at the first surface 456 of the cover plate 448, having a second larger diameter. A shoulder or ledge 478 is, therefore, disposed between the first and second parts of the hole 474, 476. The ledge 478 provides a seat for receiving a second seal element such as an O-ring 79, as shown most clearly in FIG. 43.

Figure 32:
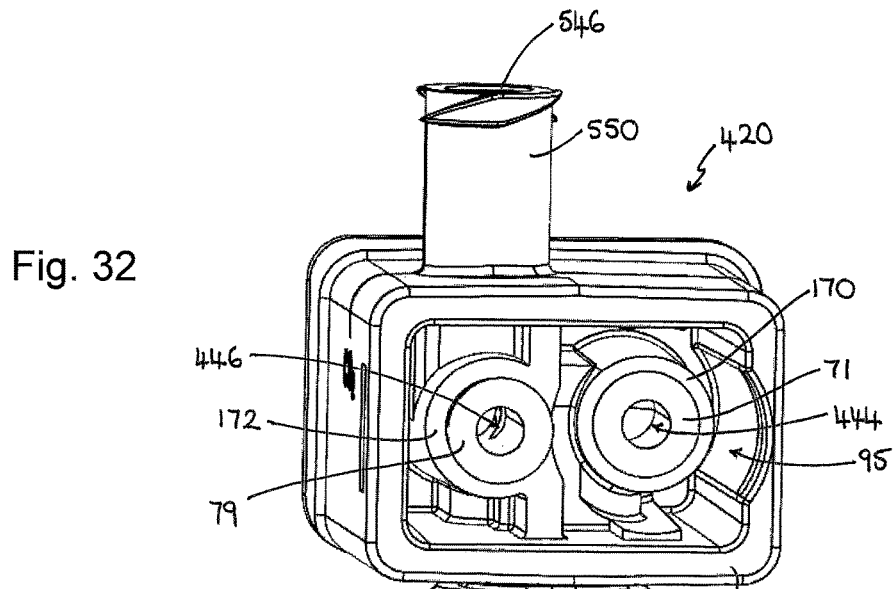
FIG. 32 is a perspective view of a main body of the fluid conduit module of FIG. 22.
Figure 43:
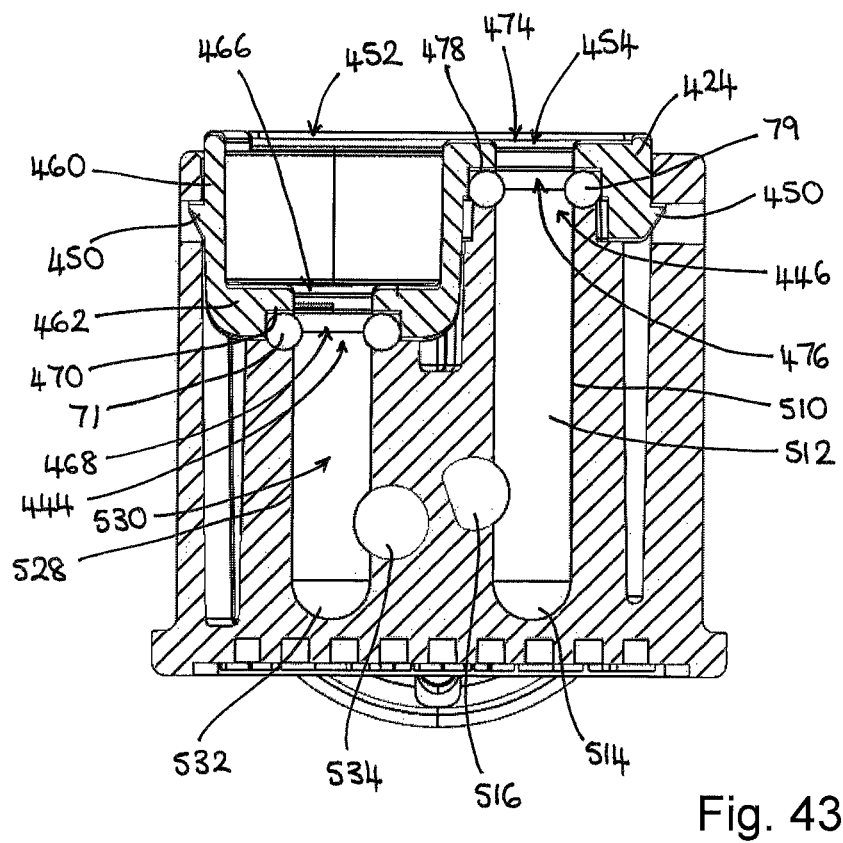
FIG. 43 is a cross-sectional view along the line XLIII-XLIII of FIG. 26.
Figure 44:
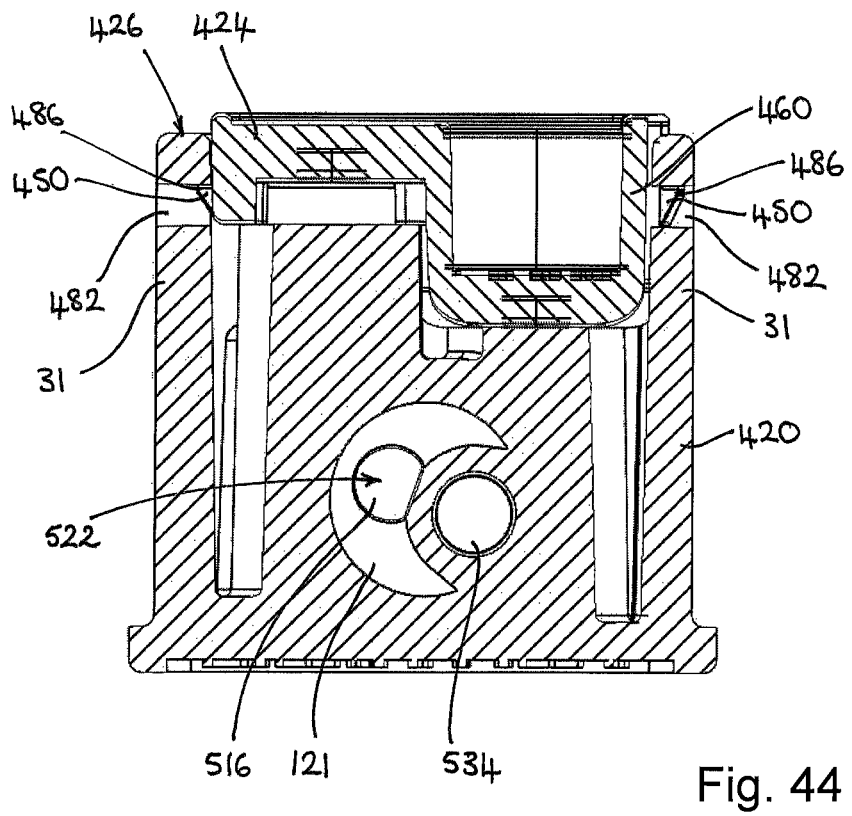
FIG. 44 is a cross-sectional view along the line XLIV-XLIV of FIG. 26.
Figure 45:
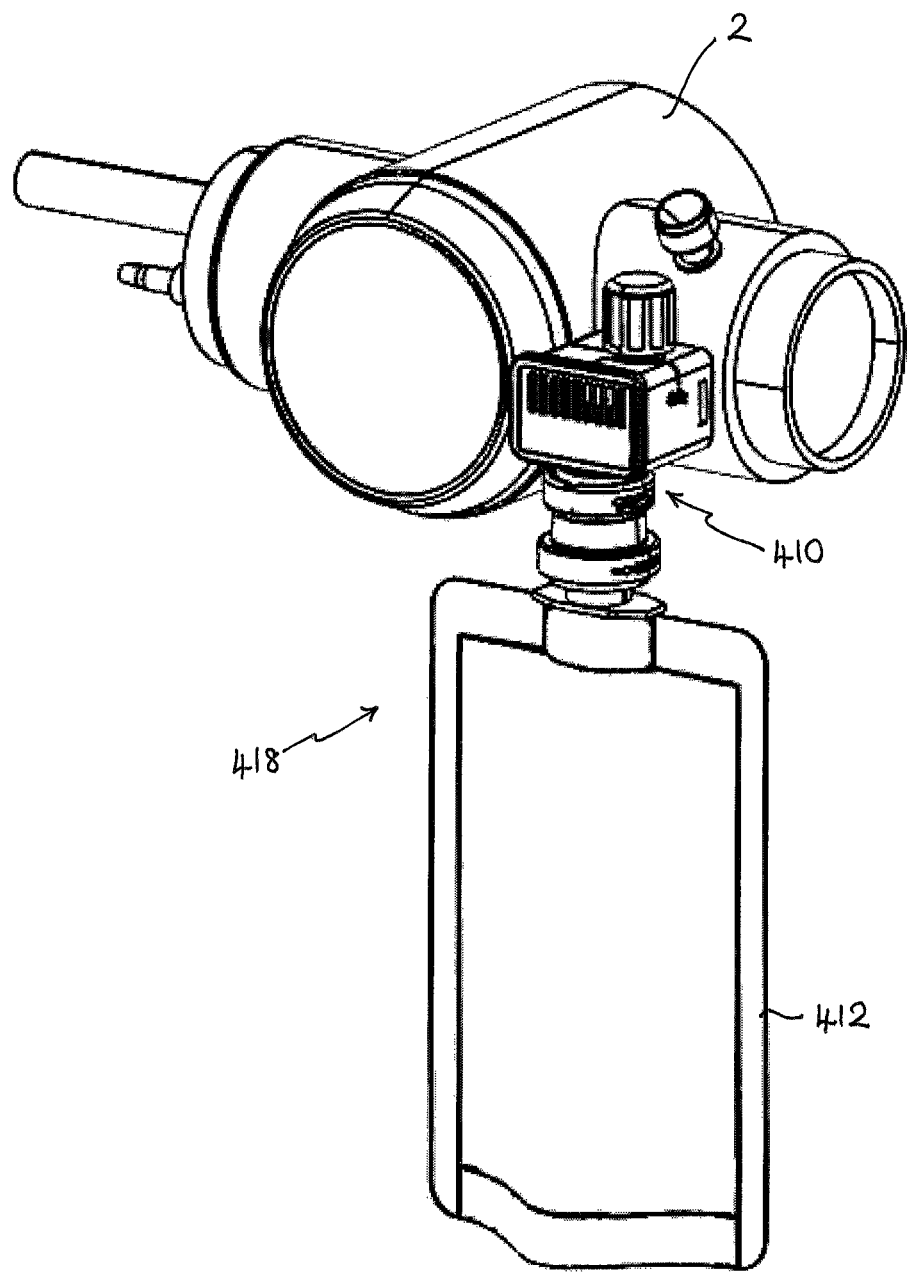
FIG. 45 shows the fluid conduit module and receptacle of FIG. 22 attached to part of an endoscope.

Referring now to FIGS. 32, 43 and 44, the main body 420 includes a first sealing surface 170 including an aperture 444 and a second sealing surface 172 including an aperture 446. When the cover 424 is engaged with the main body 420, the aperture 444 aligns with the hole 464 in the cover 424, and the first seal element 71 is disposed between the ledge 470 and the first sealing surface 170 to form a fluid tight seal between the main body 420 and the cover 424 surrounding the aligned first hole 464 and aperture 444. Similarly, the aperture 446 aligns with the second hole 454 in the cover 424, and the second seal element 79 is disposed between the ledge 478 and the second sealing surface 172 to form a fluid tight seal between the main body 420 and the cover 424 surrounding the aligned second hole 454 and aperture 446.

When the cover 424 is engaged with the main body 420 to form the complete fluid conduit module 410, the aligned second hole 454 and aperture 446 forms the first port 414 of the module 410 for connection to an air line of an endoscope 2 and the aligned first hole 464 and aperture 444 forms the second port 416 of the module 410 for connection to a water line of an endoscope 2. The O-rings 79, 71 provide gas and water tight seals between the protruding gas and water ports on the endoscope 2 and the first and second ports 414, 416 of the fluid conduit module 410, respectively.

In this embodiment a rim or lip 494 extends around the periphery of the front face 426 of the main body 420 and defines the opening 95 in the front face 426. When the cover 424 is engaged in the opening 95 of the main body 420, the rim 494 surrounds sides of the cover 424.

As shown most clearly in FIG. 44 the main body 420 comprises a latch recess 482 configured to engage with the latch member 450 of the cover 424. In particular the main body 420 includes a pair of latch recesses 482 in end walls 31 of the main body 420 proximate the front face 26 of the main body 420. In this embodiment the latch members 450 comprise protrusions 486 extending from opposite sides or ends of the cover plate 448, as shown most clearly in FIG. 34. Each protrusion has a substantially triangular cross-sectional shape and includes a leading sloped surface and a latch surface.

When the cover 424 is engaged in the opening 95 of the main body 420, each of the latch members 450 engages with a respective one of the latch recesses 482. Preferably the latch members 450 are a snap fit into the latch recesses 482, and the protrusions 486 are configured such that the protrusions 486 cannot be subsequently disengaged from the recesses 482 to remove the cover 424. It will be appreciated that in other embodiments different types of latch mechanism may be used to retain the cover 424 in the opening 95 of the main body 420.

As shown most clearly in FIGS. 27 to 31, 35 and 41, the connector assembly 422 comprises a connector member 174 and a locking collar 99. A tubular attachment member 176 extends from the bottom face 434 of the main body 420. When the container 418 is fully assembled, the locking collar 99 is secured to the attachment member 176, and the connector member 174 is secured to the locking collar 99. The engagement of the locking collar 99 with both the attachment member 176 and the connector member 174, and the configuration of the locking collar 99, is such that the connector member 174 cannot subsequently be detached from the locking collar 99 and the locking collar 99 cannot subsequently be detached from the main body 420 without disabling a part of the connector assembly 422 such that the container 418 cannot be reused.

The attachment member 176 comprises an annular wall 177 surrounding a central bore 178. The attachment member 176 comprises a proximal end region and a distal end region. The bore 178 has a first, smaller diameter in the proximal end region of the attachment member 176 and a second, larger diameter in the distal end region.

A weakened section 506 is provided between a proximal end of the annular wall 177 and the bottom face 434 of the main body 420. As shown most clearly in FIG. 39, the weakened section 506 comprises an annular side wall 107 surrounding a bore. The bore of the weakened section 506 has the same diameter as and is continuous with the bore 178 at the proximal end of the annular wall 177. An external diameter of the annular side wall 107 of the weakened section 506, however, is smaller than an external diameter of the annular wall 177 at the proximal end of the annular wall 177. In this way, an annular groove 109 is effectively provided in an external surface of the attachment member 176 at the proximal end of the attachment member 176.

Figure 41:
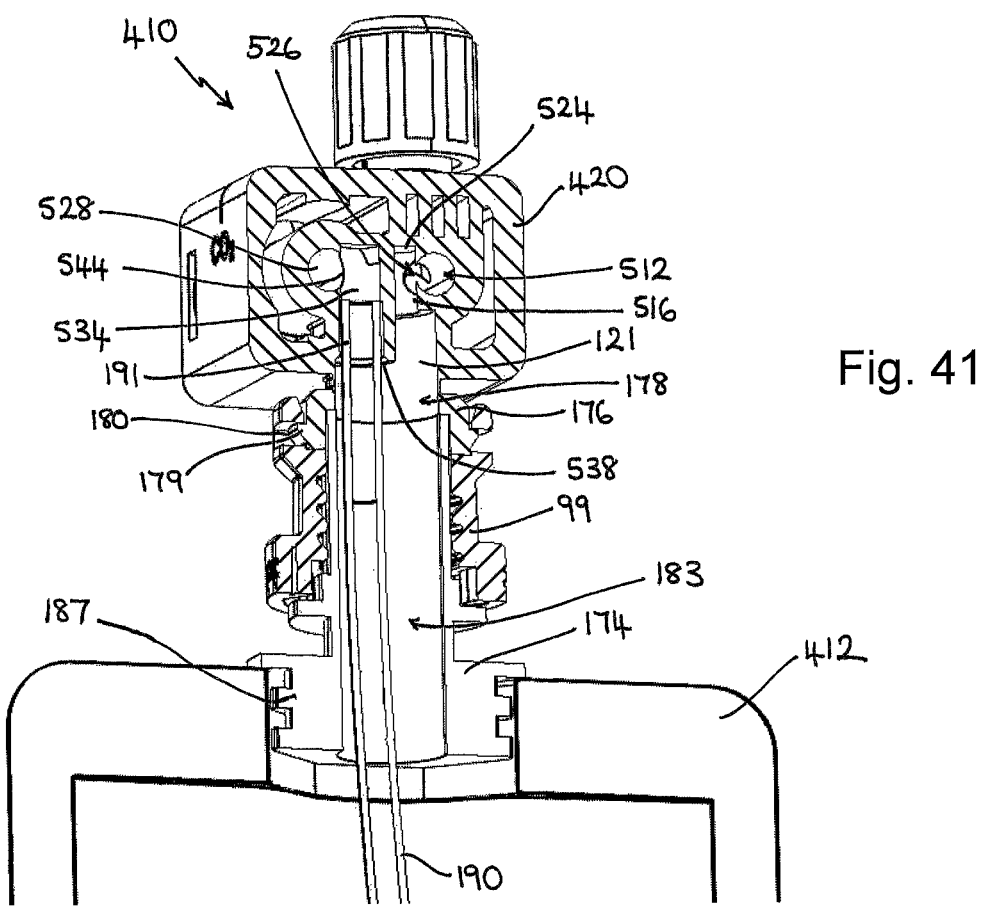
FIG. 41 is a sectioned perspective view along the line XLI-XLI of FIG. 22.
Figure 42:
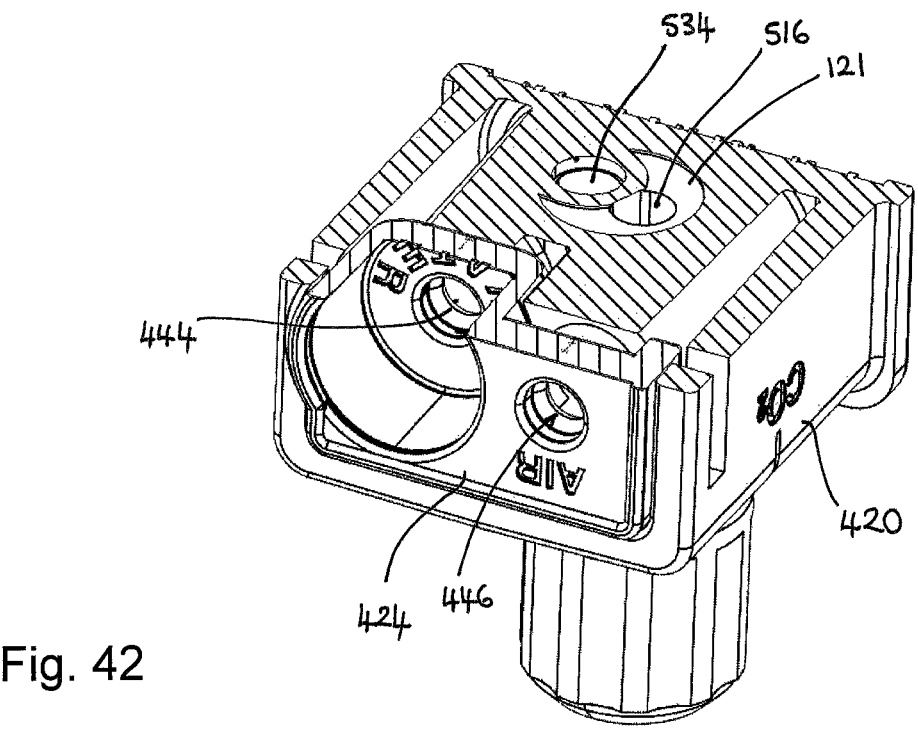
FIG. 42 is a sectioned perspective view along the line XLII-XLII of FIG. 35.

The bore of the weakened section, and therefore also the bore 178 of the attachment member, is aligned with and continuous with an opening 121 in the bottom face 434 of the main body 420 (see FIG. 41).

A pair of latch members 179 extend from an outer surface of the annular wall 177 proximate a distal end of the annular wall 177. Each latch member 179 has a substantially triangular cross-sectional shape and includes a leading sloped surface and a latch surface. The latch members 179 are configured to engage with locking apertures 180 in the locking collar 99.

The locking collar 99, shown most clearly in FIGS. 30, 31, 39 and 40, comprises a tubular member 496 extending between a first end 95 and a second end 97. An internal surface 498 of the tubular member 496 is threaded for engagement with a part of the connector member 174 as described further below.

The locking apertures 180 are provided in a latch ring 181 at the first end 95 of the tubular member 496. In this embodiment the latch ring 181 is in the form of a cylindrical collar or flange extending longitudinally from the first end 95 of the tubular member 496. The latch ring 181 is configured to engage with the distal end region of the attachment member 176. As such, the latch ring 181 has an internal diameter substantially the same as or slightly larger than the external diameter of the distal end of the annular wall 177 of the attachment member 176.

A ratchet ring 500 is disposed at the second end 97 of the tubular member 496. The ratchet ring 500 comprises an annular outer member 502 and a plurality of ratchet teeth 504 that are spaced around the outer member 502 and extend inwardly from the outer member 502. The ratchet teeth 504 extend from the outer member 502 at an angle that is not perpendicular to outer member 502. The angled ratchet teeth 504 allow the locking collar 99 to be screwed onto the connector member 174 (as described below) but prevent or guard against the locking collar 99 being unscrewed and removed from the connector member 174.

Figure 29:
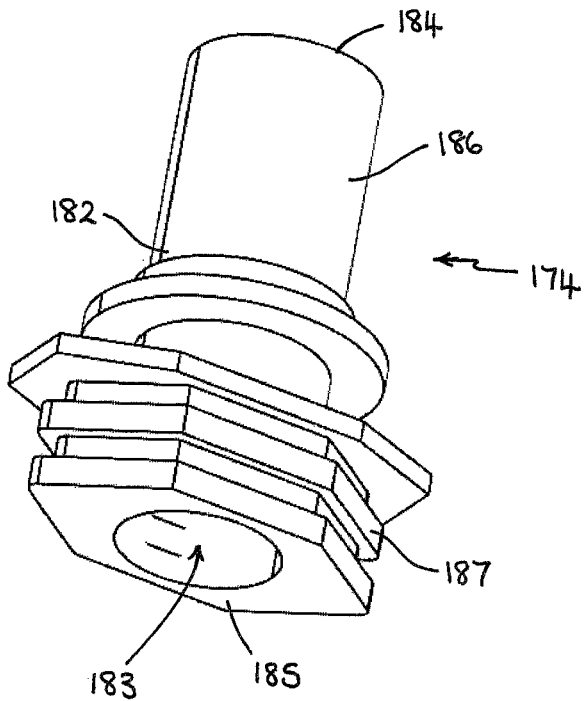
FIG. 29 shows a connector member of the fluid conduit module of FIG. 22.
Figure 30:
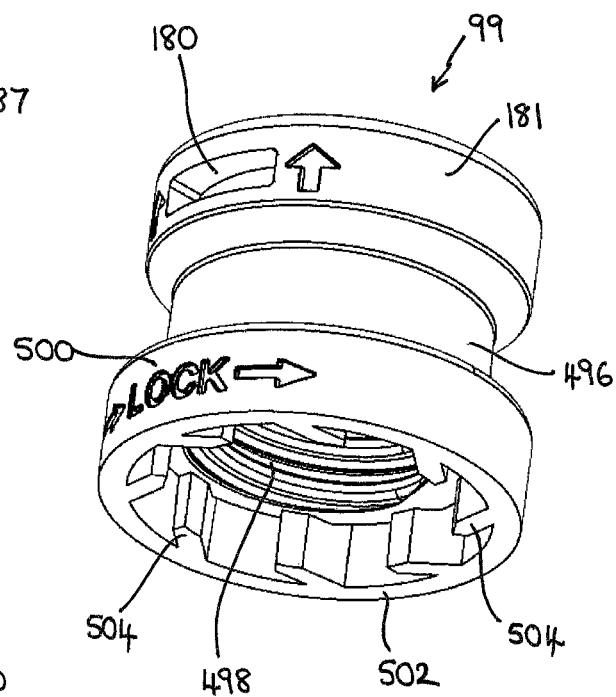
FIGS. 30 and 31 show a locking collar of the fluid conduit module of FIG. 22.
Figure 31:
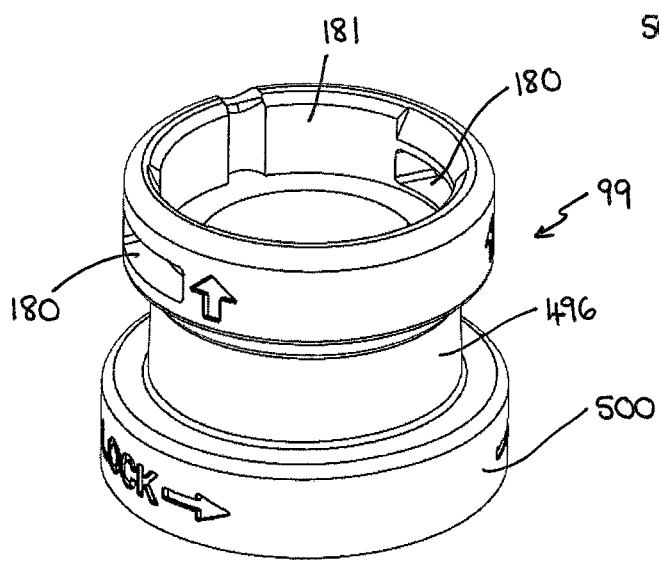

The connector member 174, shown most clearly in FIG. 29, comprises an elongate cylindrical member 182 having a central bore 183 extending between first and second ends 184, 185 of the cylindrical member 182. The cylindrical member 182 comprises a first end region 186 and a second end region 187. The first end region 186 includes an external thread for engagement with the threaded internal surface 498 of the tubular member 496. The second end region 187 is configured for welding or otherwise securing to a suitable receptacle such as a pouch.

It will be appreciated that, although the connector member 174 is described as forming part of the connector assembly 422 in this embodiment of the fluid conduit module 410, in other embodiments the connector member may be part of a pre-filled receptacle that is subsequently secured to the locking collar of the connector assembly. The connector member may be in the form of a spout connected to a receptacle or pouch. Accordingly, in these embodiments the fluid conduit module comprises the main body and the locking collar, while the connector member forms part of the receptacle attachable to the fluid conduit module.

In other embodiments the complete connector assembly (i.e. both the connector member and the locking collar) may form part of a nozzle attached to the receptacle. The nozzle may be attached to a pre-filled receptacle by heat welding. In these embodiments the connector assembly is preferably a unitary connector having a proximal end attached to the pouch and a distal end configured to be secured to the main body of the fluid conduit module. In preferred embodiments the distal end of the connector comprises a latch ring configured to engage with the attachment member 176 of the main body 420, as described above. It will be appreciated that the latch ring is configured such that once the connector has been attached to the attachment member 176, the connector cannot be removed from the attachment member 176 without disabling or breaking one of the attachment member 176 or the connector. In these embodiments, therefore, the fluid conduit module is formed by the main body and the locking collar after the receptacle has been attached to the main body.

If a user tries to unscrew the fluid conduit module 410 from the receptacle 412, the ratchet ring 500 hinders relative rotation of the locking collar 99 and connector member 174. If a user applies a greater twisting force to the module 410 to try and overcome the ratchet ring 500 and unscrew the module 410 from the receptacle 412, the weakened section 506 breaks or shears, such that the module 410 becomes unusable.

These features, therefore, guard against a user removing the module 410 from the receptacle 412 to refill the receptacle 412 and use it a second time. The connector portion 422 is, therefore, single-use.

The configuration of the fluid conduits within the module 410 of this embodiment will now be further described with particular reference to FIGS. 40 to 44.

A first fluid conduit 510 extends through the main body 420 from the aperture 446. The first fluid conduit 510 extends substantially perpendicular to the front face 426 of the main body 420. A bore 512 of the first fluid conduit 510 is closed at a second end 514 furthest from the aperture 446. The second end 514 of the conduit 510 is curved and preferably has a hemi-spherical shape. In other embodiments the closed end of the bore 512 may be sloped or chamfered such that an end wall of the conduit 510 is not perpendicular to an axis of the bore 512.

A second fluid conduit 516 extends through the main body 420 in a direction substantially perpendicular to the first fluid conduit 510. The first and second fluid conduits 510, 516 intersect such that fluid may flow through the first conduit 510 and into the second conduit 516. Importantly, the second fluid conduit 516 is offset from the first fluid conduit 510 such that a part of a side wall of the second fluid conduit 516 intersects a part of a side wall of the first fluid conduit 510. In this way an intersection 526 is formed between the first and second conduits 510, 516 permitting fluid flow between the first and second fluid conduits 510, 516, and the fluid flow through the intersection 526 is substantially perpendicular to the axes of both the first and second conduits 510, 516. The intersection 526 is preferably at a distance from the closed end 514 of the first fluid conduit 510.

A first end of the conduit 516 is in fluid communication with the opening 121 in the main body 420. A bore 522 of the second fluid conduit 516 is closed at its second end 524 furthest from the opening 121. In this embodiment an end wall of the conduit 516 at the second end 524 is substantially perpendicular to an axis of the bore 522.

A third fluid conduit 528 extends through the main body 420 from the aperture 444. The third fluid conduit 528 extends substantially perpendicular to the front face 426 of the main body 420. A bore 530 of the third fluid conduit 528 is closed at a second end 532 furthest from the aperture 444. The second end 532 of the conduit 528 has a convex curvature and preferably has a hemi-spherical shape. In other embodiments the closed end 532 of the bore 530 may be sloped or chamfered such that an end wall of the conduit 528 is not perpendicular to an axis of the bore 530. The third fluid conduit 528 preferably extends substantially parallel to the first fluid conduit 510.

A fourth fluid conduit 534 extends through the main body 420 in a direction substantially perpendicular to the third fluid conduit 528 and preferably extends substantially parallel to the second fluid conduit 516. A first end 536 of the conduit 534 terminates in an opening 538 proximate the bottom face 434 of the main body 420. The opening 538 is disposed within the opening 121 in the main body 420. A bore 540 of the fourth fluid conduit 534 is closed at its second end 542 furthest from the opening 538. In this embodiment an end wall of the conduit 534 is substantially perpendicular to an axis of the bore 540.

The third and fourth fluid conduits 528, 534 intersect such that fluid may flow through the third conduit 528 and into the fourth conduit 534. Importantly, the fourth fluid conduit 534 is offset from the third fluid conduit 528 such that a part of a side wall of the fourth fluid conduit 534 intersects a part of a side wall of the third fluid conduit 528. In this way an intersection 544 is formed between the third and fourth conduits 528, 534 permitting fluid flow between the third and fourth fluid conduits 528, 534, and the fluid flow through the intersection 544 is substantially perpendicular to the axes of both the third and fourth conduits 528, 534. The intersection 544 is preferably at a distance from the closed end 532 of the third fluid conduit 528.

Attempts to refill the receptacle 412 by injecting water into either one of the first and third conduits 510, 528 will result in the liquid being ejected back out of the bore 512, 530 as it rebounds off the closed end 514, 532 of the conduit 510, 528. Furthermore, the offset nature of the intersecting conduits 510, 516, 528, 534 results in it being very difficult to force water down one of the second and fourth conduits 516, 534 and into the receptacle 412.

In this embodiment the fluid conduit module 410 further comprises a gas port 546 permitting a gas, such as carbon dioxide ($CO_2$), to be pumped through the fluid conduit module 410.

The gas port 546 comprises an inlet 548 formed by a cylindrical tube 550 extending from the top face 432 of the main body 420. The inlet 548 preferably comprises a closure allowing the inlet 548 to be sealed or closed when not in use. In this embodiment the cylindrical tube 550 is configured to engage with a standard Luer Lock cap 551.

The cylindrical tube 550 surrounds an opening 552 in the top face 432 of the main body 420. A fifth fluid conduit 554 extends through the main body 420 from the opening 552. The fifth fluid conduit 554 extends in a direction substantially perpendicular to the top face 432. Preferably the fifth fluid conduit 554 extends in a direction substantially perpendicular to the first fluid conduit 510. A second end 556 of the fifth fluid conduit 554 intersects the first fluid conduit 510 forming an intersection 558 such that fluid is able to flow from the fifth fluid conduit 554 into the first fluid conduit 510.

The intersection 558 between the fifth and first conduits 554, 510 is preferably offset from the intersection 526 between the first and second conduits 510, 516 along the length of the first conduit 510. Also the fifth and second conduits 554, 516 are preferably offset from each other such the intersection 558 between the fifth and first conduits 554, 510 and the intersection 526 between the first and second conduits 510, 516 are at approximately 90° to each other. In this way attempts to inject water through the gas port 546 into the receptacle 412 will be frustrated by the offset nature of the fifth conduit 554 and the second conduit 516. Water will more readily flow out of the first conduit 510 than flow into the receptacle 412 through the second conduit 516.

A length of tubing 190 is connected to the main body 420 such that the tubing 190 is in fluid communication with the fourth conduit 534. In this embodiment a proximal end 191 of the tubing 190 is disposed in the bore 540 of the fourth fluid conduit 534, such that the tubing extends through and out of the opening 538. The tubing 190 extends through the opening 121 of the main body 420, through the bore 178 of the attachment member 176, and through the bore 183 of the connector member 174.

When the fluid conduit module 410 is attached to a receptacle 412, the tubing 190 extends into the interior volume of the receptacle 412. Preferably a distal end 193 of the tubing 190 is disposed near a base or end of the receptacle 412. The distal end 193 of the tubing 190 may be angled to ensure that the opening at the distal end 193 of the tubing 190 does not become occluded by an internal surface of the receptacle 412 or pouch. In preferred embodiments an end face of the tubing 190 at the distal end 193 of the tubing may extend at approximately 45° to an axis of the tubing 190. Preferably the tubing 190 is flexible.

In use, to dispense liquid from the receptacle 412 into the endoscope 2, air from the air line of the endoscope 2 is forced through the first port 414 of the module 410. The air flows through the first and second fluid conduits 510, 516 in the module 410 and into the receptacle or pouch 412 through the opening 121, through the bore 178 of the attachment member 176, and through the bore 183 of the connector member 174. This increases the pressure in the pouch 412. The pressure will typically increase to a maximum of about 5 psi. The increased pressure forces liquid out of the pouch 412 through the tubing 190, and through the fourth fluid conduit 534 and the third fluid conduit 528 in the module 410. The liquid then flows out of the second port 416 and into the water line of the endoscope 2. The tubing 190 permits all of the liquid (for example sterile water or detergent) within the pouch 412 to be used as the end of the tubing 190 sits or lies proximate or at the base of the receptacle 412.

The fluid conduit module 410 is preferably made of polypropylene, but may be made of any suitable polymeric material.

The fluid conduit module 410 may include a removable sheet (not shown) that extends over the second surface 458 of the cover plate 448. In these embodiments the removable sheet extends over and covers both of the holes 452, 454 formed through the cover plate 448 and seals both the first and second ports 414, 416. Prior to use of the fluid conduit module 410, the sheet is removed to allow access to the first and second ports 414, 416. The sheet is preferred attached to the cover 424 by a suitable adhesive such that the sheet can be peeled apart from the cover 424.

Although in the embodiments described above a separate length of tubing 190 was connected to the main body 20, 420 in fluid communication with the fourth conduit 134, 534, it will be appreciated that in other embodiments the tubing may, at least partially, be integrally formed with the main body, 20, 420. The complete length of tubing may be integrally formed with the main body. In other embodiments a first section of the length of tubing may be integrally formed with the main body. A distal end of the first section of tubing may include a connection feature configured to enable the first section to be connected to a second section of tubing to form the complete length of tubing.

In some embodiments the inlet of the gas port may be configured to permit a gas (such as carbon dioxide ($CO_2$)) to flow through the inlet but prevent a flow of liquid (such as water) through the inlet. The inlet of the gas port may comprise a suitable gas-permeable membrane. In other embodiments the inlet may comprise a tube with a bore having a tortuous flow path. This may readily permit the flow of gas through the inlet but may impede or restrict the flow of liquid through the inlet. The inlet may be shaped or configured to prevent insertion of a tip of a needle or syringe having sufficient diameter to easily inject a liquid through the inlet. This will impede or restrict a user trying to refill the receptacle by injecting a liquid through the gas port and associated inlet.

In the above embodiments O-rings (or other suitable sealing elements) were supported on shoulders or ledges 70, 78, 470, 478 provided in the cover plate 48, 448 and were confined between the cover plate 48, 448 and the front face 26, 426 of the main body 20, 420 when the cover or cover portion 24, 424 is secured in its closed position. In use, the O-rings then form the required gas-tight and liquid-tight seals between the first and second ports 14, 16, 414, 416 of the fluid conduit module 10, 410 and the air and water ports of the endoscope 2, respectively. It will be appreciated, however, that it may be preferable to more securely mount the O-rings (or other sealing elements) to the cover plate to assist in retaining the O-rings in position when the cover or cover portion is secured to the main body in its closed position. In some embodiments it may be desirable to provide a suitable retaining feature in the cover plate, such as a clip or undercut in which or under which a part of the O-ring is seated or located. In other embodiments the sealing element may be overmoulded onto the cover plate. In these embodiments a layer of elastomeric material may be overmoulded onto the shoulder or ledge of the cover plate.

The present invention therefore provides an improved fluid conduit module for attachment to a receptacle that permits liquid to be supplied to the water line of an endoscope, and which is single use, thereby minimising the risk of cross-contamination.

The invention claimed is:

1. A fluid conduit module for connecting a receptacle to an endoscope, said receptacle having an internal volume for holding a liquid, and the fluid conduit module comprising:
   a first port for connection to an air line of an endoscope;
   a second port for connection to a water line of an endoscope;
   a connector configured to attach said receptacle to the fluid conduit module;
   a first fluid flow path between the first port and the connector; and
   a second fluid flow path between the second port and the connector,
   wherein the connector is configured such that, in use, when a receptacle is connected to the fluid conduit module, the first and second fluid flow paths are in fluid communication with said internal volume of the receptacle, and
   wherein the fluid conduit module comprises a first single use feature configured to disable the connector to prevent attachment of a second receptacle after use of a first receptacle and a second single use feature configured to hinder or prevent refilling of the receptacle via the first and second flow paths,
   wherein the first single use feature comprises a weakened part of the connector that is configured to rupture if, in use, a force is applied to the connector to detach the connector from said receptacle.

2. The fluid conduit module as claimed in claim 1, in which the fluid conduit module is configured such that the connector is in a fixed position relative to the first and second ports.

3. The fluid conduit module as claimed in claim 1, wherein the connector comprises a screw thread for attachment to a complementary screw thread of said receptacle.

4. The fluid conduit module as claimed in claim 3, in which the connector comprises a ratchet mechanism configured to allow a receptacle to be secured to the connector but to prevent a receptacle being detached from the connector.

5. The fluid conduit module as claimed in claim 1, in which the first fluid flow path further comprises a first fluid conduit extending between the first port and a closed end and a second fluid conduit extending between a first opening in the connector and a closed end, the second fluid conduit extending substantially perpendicular to the first fluid conduit, and the second fluid flow path further comprises a third fluid conduit extending between the second port and a closed end and a fourth fluid conduit extending between a second opening in said connector and a closed end, the fourth fluid conduit extending substantially perpendicular to the third fluid conduit, such that attempts to refill the receptacle by injecting liquid into either one of the first conduit or third conduit will result in the liquid being ejected back out of the conduit as it rebounds off the closed end of the first conduit or the third conduit thereby hindering or preventing refilling of the receptacle via the first and second flow paths.

6. The fluid conduit module as claimed in claim 5, in which a first intersection permits fluid flow between the first and second fluid conduits, the first intersection being at a distance from the closed end of the first fluid conduit, and the first and second fluid conduits are offset such that the direction of fluid flow through the first intersection is substantially perpendicular to axes of both the first and second conduits, and a second intersection permits fluid flow between the third and fourth fluid conduits, the second intersection being at a distance from the closed end of the third fluid conduit, and the third and fourth fluid conduits are offset such that the direction of fluid flow through the second intersection is substantially perpendicular to axes of both the third and fourth conduits.

7. The fluid conduit module as claimed in claim 1, further comprising a length of tubing extending from the connector and being in fluid communication with the second fluid flow path.

8. The fluid conduit module as claimed in claim 1, comprising a main body including first and second apertures and a cover including first and second holes, the main body including an opening in which the cover is received such that the first hole aligns with the first aperture to form the second port of the fluid conduit module and the second hole aligns with the second aperture to form the first port of the fluid conduit module.

9. The fluid conduit module as claimed in claim 8, in which the main body includes a first sealing surface and a second sealing surface and the cover includes a first seat and a second seat, and wherein, when the cover is engaged with the main body, a first seal element is disposed between the first seat and the first sealing surface to form a fluid tight seal between the main body and the cover surrounding said aligned first hole and aperture, and a second seal element is disposed between the second seat and the second sealing surface to form a fluid tight seal between the main body and the cover surrounding said aligned second hole and aperture.

10. The fluid conduit module as claimed in claim 8, in which the cover comprises a latch member and the main body comprises a latch recess, the latch member being engaged with the latch recess when the cover is received in the opening in the main body.

11. The fluid conduit module as claimed in claim 1, the fluid conduit module being made from a polymeric material.

12. A container comprising the fluid conduit module as claimed in claim 1 and a receptacle secured to the connector of the fluid conduit module.

13. The container as claimed in claim 12, wherein the receptacle comprises a flexible pouch.

14. The container as claimed in claim 12, wherein an internal volume of the receptacle contains sterile water or detergent.

15. An assembly comprising the container as claimed in claim 12 and an endoscope, the fluid conduit module being engaged with air and water ports of the endoscope such that the container is solely suspended from the endoscope.

16. The fluid conduit module as claimed in claim 1, in which the second single use feature comprises the first fluid flow path that is tortuous and the second fluid flow path that is tortuous, the first and second fluid flow paths thereby impeding an injection of a liquid through either of the first and second ports into said receptacle.

* * * * *